(12) United States Patent
Braig et al.

(10) Patent No.: US 6,577,885 B1
(45) Date of Patent: *Jun. 10, 2003

(54) METHOD FOR DETERMINING ANALYTE CONCENTRATION USING PERIODIC TEMPERATURE MODULATION AND PHASE DETECTION

(75) Inventors: James R. Braig, Alameda, CA (US); Charles E. Kramer, Poway, CA (US); Bernhard B. Sterling, Danville, CA (US); Daniel S. Goldberger, Boulder, CO (US); Peng Zheng, Alameda, CA (US); Arthur M. Shulenberger, Brisbane, CA (US); Rick Trebino, Atlanta, GA (US); Richard A. King, Berkeley, CA (US); Casper W. Barnes, Murrieta, CA (US)

(73) Assignee: OptiScan Biomedical Corporation, Alameda, CA (US)

( * ) Notice: Subject to any disclaimer, the term of this patent is extended or adjusted under 35 U.S.C. 154(b) by 369 days.

This patent is subject to a terminal disclaimer.

(21) Appl. No.: 09/663,114

(22) Filed: Sep. 15, 2000

Related U.S. Application Data

(63) Continuation of application No. 09/267,121, filed on Mar. 10, 1999, now Pat. No. 6,161,028, which is a continuation-in-part of application No. 08/820,378, filed on Mar. 12, 1997, now Pat. No. 5,900,632.

(51) Int. Cl.⁷ .............................. A61B 5/00; G01N 21/71
(52) U.S. Cl. ................. 600/310; 600/322; 250/339.03; 250/339.07; 250/341.6
(58) Field of Search .................................. 600/309, 310, 600/316, 322, 473, 474; 250/341.6, 341.1, 341.5, 339.07, 339.09, 339.03, 339.04, 339.05, 339.12

(56) References Cited

U.S. PATENT DOCUMENTS

| 3,958,560 A | 5/1976 | March |
| 4,429,999 A | 2/1984 | Bimberg et al. |
| 4,655,225 A | 4/1987 | Dahne et al. |
| 5,009,230 A | 4/1991 | Hutchinson |
| 5,040,539 A | 8/1991 | Schmitt et al. |

(List continued on next page.)

FOREIGN PATENT DOCUMENTS

| CH | 612271 | 7/1979 |
| WO | WO 91/15992 | 10/1991 |
| WO | WO 93/00855 | 1/1993 |
| WO | WO 96/01075 | 1/1996 |

OTHER PUBLICATIONS

Barnes, Barnes Infrared Camera, Defense and Space Division Barnes Engineering Co. Bulletin 12–600, pp. 1–12 (May 1963).

(List continued on next page.)

*Primary Examiner*—Eric F. Winakur
(74) *Attorney, Agent, or Firm*—Knobbe Martens Olson & Bear LLP

(57) ABSTRACT

A method of determining the analyte concentration of a test sample is described. A temperature gradient is introduced in the test sample and infrared radiation detectors measure radiation at selected analyte absorbance peak and reference wavelengths. Reference and analytical signals are detected. In the presence of the selected analyte, parameter differences between reference and analytical signals are detectable. These parameter differences, having a relationship to analyte concentration, are measured, correlated, and processed to determine analyte concentration in the test sample. Accuracy is enhanced by inducing a periodically modulated temperature gradient in the test sample. The analytical and reference signals may be measured continuously and the parameter difference integrated over the measurement period to determine analyte concentration.

9 Claims, 20 Drawing Sheets

U.S. PATENT DOCUMENTS

| | | | |
|---|---|---|---|
| 5,070,242 | A | 12/1991 | McClelland et al. |
| 5,075,552 | A | 12/1991 | McClelland et al. |
| 5,137,023 | A | 8/1992 | Mendelson et al. |
| 5,191,215 | A | 3/1993 | McClelland et al. |
| 5,313,941 | A | 5/1994 | Braig et al. |
| 5,360,004 | A | 11/1994 | Purdy et al. |
| 5,361,758 | A | 11/1994 | Hall et al. |
| 5,370,114 | A | 12/1994 | Wong et al. |
| 5,372,135 | A | 12/1994 | Mendelson et al. |
| 5,372,136 | A | 12/1994 | Steuer et al. |
| 5,383,452 | A | 1/1995 | Buchert |
| 5,451,787 | A | 9/1995 | Taylor |
| 5,461,229 | A | 10/1995 | Sauter et al. |
| 5,471,056 | A | 11/1995 | Prelat |
| 5,473,162 | A | 12/1995 | Busch et al. |
| 5,515,847 | A | 5/1996 | Braig et al. |
| 5,615,672 | A | 4/1997 | Braig et al. |
| 5,666,956 | A | 9/1997 | Buchert |
| 5,823,677 | A | 10/1998 | Forester et al. |
| 5,900,632 | A | 5/1999 | Sterling et al. |
| 6,002,953 | A | 12/1999 | Block |

OTHER PUBLICATIONS

Dueker et al., Germanium Nonscanned Infrared Imager, IEEE Transactions on Electron Devices, vol. ED–18, No. 11, pp. 1108–1112 (Nov. 1991).

F. G. Pollack, Advances in Turbine Blade Temperature Measurements, 22nd Int'l Instrumentation Symposium, San Diego CA, ISA ASI 76256, pp. 393–398 (May 1976).

A.S. Glushkov, Thermoptical converter with liquid modulating medium, Sov. Tech. Phys. Lett. 5(10), p. 512 (Oct. 1979).

Roger W. Jones & John F. McClelland, On–line analysis of solids and viscous liquids by transient infrared spectroscopy, Process Control and Quality, 1993, pp. 253–260.

Roger W. Jones & John F. McClelland, Transient Infrared Transmission Spectroscopy, Analytic Chemistry, 1990.

Roger W. Jones & John F. McClelland, Quantitative Analysis of Solids in Motion by Transient Infrared Emission Spectroscopy Using Hot–Gast Jet Excitation, Analytic Chemistry, 1990.

Roger W. Jones & John F. McClelland, Real–Time Infrared Spectroscopy of Moving Solids for On–Line Analyses, 1991.

R. Bowling Barnes, Thermography of the Human Body, Science, May 24, 1963, vol. 140, No. 3569, pp. 870–877.

Halliday et al., Fundamentals of Physics, 2nd Ed. 1981, pp. 358–361.

O.Guillois, I.Nenner, R. Papoular, & C. Reynaud, IR Emission Spectrum of Solid materials under Peiodic Heating: Modulcated Emission Spectroscopy (MES), Applied Spectroscopy, vol. 48, No. 3, pp. 297–306 (Mar., 1994).

METHOD FOR DETERMINING ANALYTE CONCENTRATION USING PERIODIC TEMPERATURE MODULATION AND PHASE DETECTION

CROSS-REFERENCE TO RELATED APPLICATIONS

This application is a continuation of application Ser. No. 09/267,121 filed on Mar. 10, 1999, now U.S. Pat. No. 6,161,028, which is a continuation-in-part of application Ser. No. 08/820,378 filed on Mar. 12, 1997, now U.S. Pat. No. 5,900,632. This application is also related to copending application Ser. No. 09/265,195 filed on Mar. 10, 1999, which is incorporated herein by reference.

FIELD OF INVENTION

This invention relates to methods of determining the presence and concentration of analytes in a test sample. More specifically, the present invention relates to methods for non-invasively determining the analyte concentrations in human or animal subjects. Most specifically, the present invention relates to a non-invasive methods for the determination of blood glucose concentration in a human patient.

BACKGROUND OF THE INVENTION

The analysis of samples and the determination of the presence or concentration of chemical species contained therein is a common and important process in chemistry and biology. Particularly important is the analysis of biological fluids, such as blood, urine, or saliva, to determine the concentration of various constituents. Also of great importance is the measurement of the concentration of various chemical constituents embedded within biological materials, such as tissue. Chemical analysis of blood, urine, and other biological fluids is crucial to the diagnosis, management, treatment, and care of a wide variety of diseases and medical conditions. In the case of diabetes, monitoring of blood glucose levels several times a day is necessary to the efficient management of this disease in many patients. Analysis of various blood components is of importance in both the diagnosis and treatment of diseases of the circulatory system. For example, the level of various types of cholesterol in the blood has a strong correlation with the onset of heart disease. Urine analysis provides valuable information relating to kidney function and kidney disease. The concentration of alcohol in the blood is known to be related to a subject's physical response time and coordination and can provide information related to, for example, the individual's fitness to drive a motor vehicle.

Additionally, there are many instances where it is desirable to measure the local concentration of chemical constituents in tissue, either in-vivo or in-vitro. For example, in stroke victims it is important to monitor the degree of brain edema or the concentration of various metabolic chemical constituents in the brain that serve as indicators of brain function. Such indicators include fatty acid compounds, water, blood, lactates, and certain proteins and lipids. Other specific examples may include the monitoring of tissue oxygenation or tissue blood perfusion as a means to of gauging the metabolic function of a human or animal subject.

Moreover, in many applications, a "real-time" measurement of chemical concentration in biological fluids is important. Current invasive methods require that a sample of fluid be removed from a subject and then analyzed in one or more chemical tests. The tests can be expensive and require skilled technicians to remove and analyze the samples. Furthermore, the analysis of samples may have an undesirably long turn-around time. Additionally, the tests are usually made in centralized clinical laboratories with a resulting complexity of sample tracking and quality control. These circumstances create additional problems related to the potential change in the chemical composition of the fluid between extraction and analysis and, even more detrimentally, the possibility of a sample being confused with the samples of other patients.

It is also advantageous to analyze the chemical nature of sample materials without physically extracting a sample from the subject. For example, it is advantageous to examine the chemical makeup of human blood without taking a blood sample. In addition to time and cost considerations such invasive testing causes skin trauma, pain, and generates blood waste.

For all of the foregoing reasons methods of "non-invasive" testing have long been considered an attractive alternative to invasive testing. However, prior non-invasive testing methods have suffered from a number of practical drawbacks. The present invention is a method of analytical and quantitative testing for the presence of chemical species in a test sample. The method is non-invasive and has wide utility, being easily applicable to the noninvasive measurement of humans, animals, plants, or even packaged materials. Being highly versatile the method is broadly applicable to both in-vivo and in-vitro samples.

1. Brief Description of Related Art

The concept of non-invasive testing is not unknown in the art. What has been elusive is the ability of quickly, easily, cheaply and accurately conducting measurements.

Certain infrared (IR) detection techniques are known and have been used to detect the presence of chemical constituents in the blood. Specific examples include the IR detection of oxygen saturation, nitrous oxide concentration, carbon dioxide concentration, or measurement of oxidative metabolism, and blood glucose levels. The goal of these inventions is the determination of human blood chemistry. A typical present technology projects light into the body while measuring the light after it passes through the body. Comparing the input beam with an exit beam allows a rough determination of blood chemistry. Unfortunately, these techniques suffer from a number of inadequacies, most especially, tissue interference, lack of specificity, and limited accuracy. A number of prior art patents describing such techniques are set forth below.

Kaiser describes, in Swiss Patent No. 612,271, a technique for using an IR laser as a radiation source to measure glucose concentrations in a measuring cell. This technique uses venous blood passed through extra-corporeal cuvettes at high blood flow rates. This has the undesirable effect of heating the blood and requiring that the blood be removed from the patient's body. Kaiser does not describe a non-invasive technique for measuring glucose concentration.

March, in U.S. Pat. No. 3,958,560, describes a "noninvasive" automatic glucose sensor system which projects polarized IR light into the cornea of the eye. A sensor detects the rotation of this polarized IR light as it passes between the eyelid and the cornea. The rotation of polarized light is correlated to glucose concentration. Although this technique does not require the withdrawal of blood, and is thus, "noninvasive", the device may cause considerable discomfort to the patient due to the need to place it on the patient's eye. Furthermore, March does not use an induced temperature gradient or absorbance spectroscopy as does the present invention. As a result, the present invention involves no physical discomfort and is more accurate.

Hutchinson, in U.S. Pat. No. 5,009,230, describes a glucose monitor which uses polarized IR light to non-invasively detect glucose concentration in a person's blood stream. The method requires an external IR source, which is passed through a portion of the human body. However, the accuracy of measurement is limited by the wavelengths of the polarized light beam (940–1000 nm) being used. Unlike the present invention, Hutchinson relies on detected changes in the polarization of the incident light beam. Furthermore, Hutchinson does not use an induced temperature gradient as does the present invention.

Similar limitations are found in Dahne, et al., in U.S. Pat. No. 4,655,225, which describes a similar spectrophotometric technique. Dahne uses a directional external IR radiation source to emit a beam. Reflected and transmitted light from the beam is used to determine the glucose concentration. Dahne differs from other techniques in using radiation at wavelengths between 1000–2500 nm. Unlike Dahne, the present invention is not confirmed to using wavelengths between 1000–2500 nm. Dahne also does not use an induced temperature gradient as does the present invention.

Mendelson, et al., in U.S. Pat. No. 5,137,023, uses a different concept known as pulsatile photoplethysmography to detect blood analyte concentration. The instrument of Mendelson is based on the principles of light transmission and reflection photoplethysmography, whereby analyte measurements are made by analyzing either the differences or ratios between two different IR radiation sources that are transmitted through an appendage or reflected from tissue surface before or after blood volume change occurs in response to systolic and diastolic phases of the cardiac cycle. Once again, the technique requires the use of external IR sources and is susceptible to interference from body tissue and other blood compounds.

Rosenthal, et al., in U.S. Pat. No. 5,028,787, discloses a non-invasive blood glucose monitor which also uses IR energy in the near IR range (600–1100 nm) to measure glucose. As with the above-mentioned devices, these wavelengths suffer from poor analyte absorption which results in poor resolution and insufficient specificity.

Cho, et al., in PCT No. PCT/DE95/00864, discloses a blood glucose monitor which uses heat flux generated in a patients fingertip to measure metabolic rate. Indirectly, this approximation of metabolic rate is used to measure approximate glucose concentration.

Major steps forward are embodied in the glucose measuring techniques disclosed in the patents to Braig, et al., U.S. Pat. No 5,313,941 ('941). However, the '941 patent requires an independent external IR source to determine blood analyte concentration.

Optiscan, Inc of Alameda, Calif. has expanded the concept of gradient absorbance spectroscopy and demonstrated the utility of non-invasively measuring differential absorbance to determine blood glucose concentration in human subjects in Pat. Applications 08/816,723 and 08/820,378, both of which are hereby incorporated by reference.

2. Scietific Background of the Invention

An understanding of the present invention requires an understanding of the concepts of transmission spectroscopy and gradient spectroscopy.

Basic transmission spectroscopy identifies analytes (an analyte is defined as a chemical species sought to be identified by the present invention) by comparing a light beam passed through a test sample to a reference beam not passed through the sample. Typically, transmission spectroscopy requires the test sample be removed from its native environment to a sample holder for analysis. The absorbance spectrum of the sample is examined. At specific wavelengths (known as analyte absorbance peaks) the light from the beams are compared. By using Beer's Law and comparing the sample beam with the reference beam in selected absorbance regions the absorbance of a sample may be measured and a determination of analyte concentration may be made. This is known as classical transmission cell spectroscopy. Strictly speaking, this method is unsuitable for non-invasive measurement. Significant problems being the need for extracting samples and the inability to accurately determine the pathlength of the beams used to analyze in-vivo samples. Progress has been made in overcoming these limitations as shown in the patents to Braig, et al., in Pat. No. 's '941, '847, and '672 and in the Pat. Appl's 08/816,723 and 08/820,378. These patents and patent applications have laid the groundwork for the novel advances embodied in the present invention and are hereby incorporated by reference.

An understanding of the radiation emission characteristics of matter are also needed. All objects at a temperature greater than 0° K emit electromagnetic radiation in the form of photons. Ideal blackbody radiators (objects having an emissivity coefficient $e_m$=1.0) radiate energy according to the Stefan-Boltzmann Law and Planck's Equation (i.e. radiation output increases with increasing temperature). Additionally, many non-blackbody objects demonstrate near-blackbody radiation characteristics. For example, the human body's spectral radiation characteristics are very similar to that of a blackbody radiator and may be described as a "graybody" distribution (for example, having an $e_m$ of about 0.9). These radiative characteristics provide known sources of IR radiation which may be used to non-invasively analyze the constituents of a test sample.

Furthermore, an analysis of radiation behavior shows that, in objects at a constant and uniform temperature, photons emitted from the interior of the object are reabsorbed within 10–20 $\mu$m of the point of origin. Thus, an external radiation detector cannot detect radiation emitted from deeper than 20 $\mu$m inside an object. Under these conditions, only an object's surface emission spectrum is detectable by a detector. This poses a significant problem for non-invasive measurement techniques seeking to analyze chemical characteristics present deeper within an object.

The field of gradient spectroscopy was developed, in part, in an attempt to overcome the photon reabsorption problem. The Optiscan patent applications 08/816,723 and 08/820,378 disclose a thermal gradient, induced by a single temperature event and a measurement of differences in signal magnitude to non-invasively measure human test samples. The Optiscan applications use a temperature gradient induced by a single temperature event to non-invasively determine the glucose concentration in a human test subject by analyzing differences in signal magnitude at selected wavelengths.

In the absence of a temperature gradient, emitted photons are reabsorbed by a test sample, after they travel only a short distance. By inducing a temperature gradient in a test sample, photons travel greater distances before reabsorption by the sample. This allows radiation emitted from deep inside the sample to reach the surface where it can be detected by a radiation detector. Additionally, the larger the gradient, the greater the detector signal is, improving the signal-to-noise ratio. The present invention utilizes this phenomenon to analyze the chemical composition of the sample without the need to pass an externally applied light beam completely through the sample.

Briefly, in the context of the present invention, a temperature gradient exists where the temperature of a material varies according to some arbitrary function, usually related to depth or time or both. For example, if some material is at an initial temperature (e.g., 37° C.) and a surface of the material is cooled to some lower temperature (e.g., 10° C.) a gradient is induced in the material with the cooled surface being at approximately 10° C. and the deeper (and as yet unaffected) regions being at approximately 37° C. A temperature gradient exists between the two extremes.

The present invention integrates all of the above-mentioned concepts to provide a method of analyzing the constituents of a test sample.

OBJECTS OF THE INVENTION

Accordingly, an object of the present invention is to provide a new and improved method for detecting and quantifying various chemical analytes present within a test sample. In particular, an object of the present invention is to determine the absolute or relative concentration of chemical species contained in a test sample medium. Another object of the present invention to provide a non-invasive method of quantifying various chemical analytes within biological media.

A specific object of the invention is to provide a new and improved method for measuring the concentration in human, animal, and plant subjects of chemical species, such as glucose, insulin, water, carbon dioxide, alcohol, blood oxygen, cholesterol, bilirubin, ketones, fatty acids, lipoproteins, albumin, urea, creatinine, cytochrome, various proteins and chromophores, microcalcifications, and hormones, white blood cells, red blood cells, hemoglobin, oxygenated hemoglobin, carboxyhemoglobin, organic molecules, inorganic molecules, and inorganic molecules, such as phosphorus or various drugs and pharmaceuticals in blood, urine, saliva, or other body fluids. A further object of the invention is to make such measurements non-invasively, quickly, easily, and with extreme accuracy.

BRIEF SUMMARY OF THE INVENTION

The present invention describes a method for quantitatively determining the chemical composition of a test sample. Test samples may be chosen from a broad range of in-vivo or in-vitro samples. The present method uses a radiation detector, a data processing means, and a means for inducing a periodic thermal gradient in the test sample. The method generally comprises the steps of providing a test sample, inducing a thermal gradient in the sample, using the detector for measuring analytical signals from the sample at one or more predetermined wavelengths. Simultaneously, one or more reference signals are measured at reference wavelengths. The analytical and reference signals are compared to determine a parameter. The parameter may be phase difference, signal amplitude difference, or frequency difference. The parameter information is correlated with empirically determined analyte concentration information by the data processing means, thereby determining the analyte concentration of the sample. This information is transmitted as an electrical signal for further processing.

A particularly useful parameter is a measurement of the phase difference (or phase delay) between said analytical and one or more of said reference signals. The magnitude of the phase difference is correlated with data stored in a data processing means to determine analyte concentration.

The accuracy of the method is substantially enhanced by inducing a periodically modulated temperature gradient in the sample, measuring the reference and analytical signals, continuously monitoring the parameters between the reference and analytical signals, and then integrating the parameter information over a test period. Correlation of this information with empirically determined analyte concentration information allows the analyte concentration of the sample to be determined and transmitted as an electrical signal for further processing.

Alternatively, when using a periodically modulated temperature gradient and phase difference information, the phase may be monitored at reference and analytical phase signal "zero crossings" to determine phase delay and thereby determine analyte concentration.

Additionally, the present method may be used to monitor analyte concentration at varying depths inside a test sample. This is accomplished by introducing two or more periodic temperature gradients in a sample at two or more driving frequencies. The resulting signals are processed to extract phase information and determine analyte concentration at varying depths within a sample. This has particular usefulness in analyzing analyte concentrations in test samples having non-uniform properties.

Finally, the method of the present invention may be used to non-invasively determine the blood glucose concentration of human and animal test subjects.

Other features of the invention are disclosed or made apparent in the section entitled "Detailed Description of the Invention".

BRIEF DESCRIPTION OF DRAWINGS

For a fuller understanding of the present invention, reference is made to the accompanying drawings, which detail various aspects of the invention.

Reference numbers refer to the same or equivalent parts of the invention throughout the several figures of the drawings.

DETAILED DESCRIPTION OF THE INVENTION

The present invention goes beyond the existing art by advantageously exploiting phase effects caused by induced temperature gradients to determine analyte concentration. The following example illustrates the general principles of the present invention.

A test sample containing analytes is provided. The term "test sample" shall be interpreted broadly to include any type of analytical sample. In its most basic form the sample comprises a sample medium and the chemical analytes contained therein. The term medium is broad in its application. The medium may be comprised of solids or fluids or any combination thereof. The medium may comprise biological material.

The present method may be applied to any type of material ordinarily analyzed using transmission cell spectroscopy. Biological materials such as human, animal, or plant material may be analyzed. These biological samples may be analyzed, either in-vivo or in-vitro. The method is versatile and may be applied to a wide range of samples, including but not limited to, in-vivo blood samples or in-vivo analysis of fruit contents, for example, testing grapes remaining on the vine for sugar content. Although most advantageously used as a method for non-invasively measuring analyte concentrations in living subjects, the method finds utility as a method for analyzing invasively removed samples such as blood or saliva removed from a subject and placed in a glass cuvette for analysis. The device may even be used to determine analyte concentrations in packaged meats without opening a plastic wrapper.

The method of the present invention requires an induced temperature gradient and monitoring of radiation emitted from test samples. A satisfactory means for meeting this requirement is described in the concurrently filed application having the LaRiviere, Grubman, & Payne Docket No. P855, entitled "Solid-state Non-invasive Infrared Absorption Spectrometer for the Generation and Capture of Thermal Gradient Spectra from Living Tissue".

Figure 1:
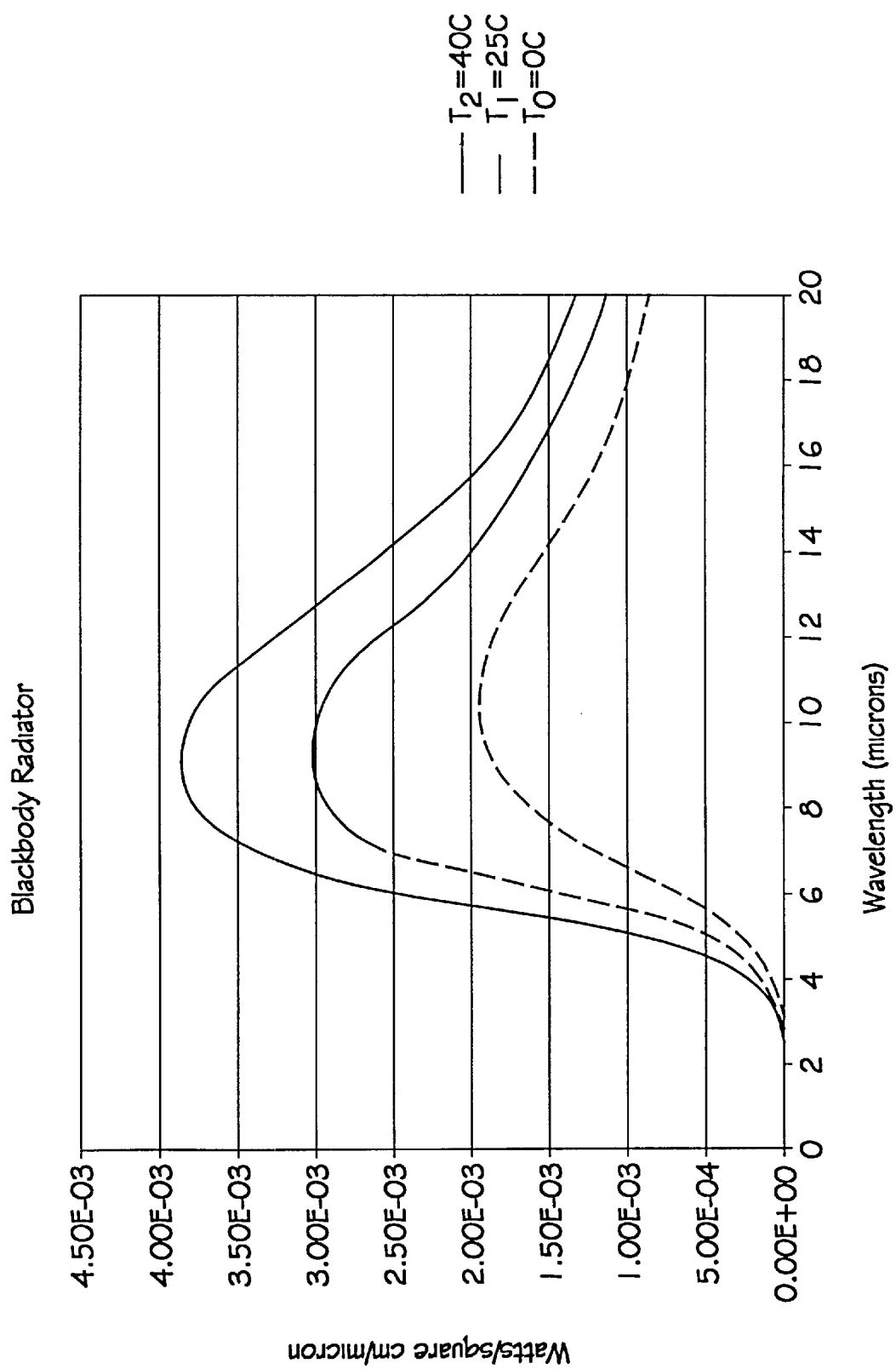
FIG. 1 is a graphical representation of the temperature effect on a blackbody radiator in units of emitted energy at a given wavelength.
Figure 2:
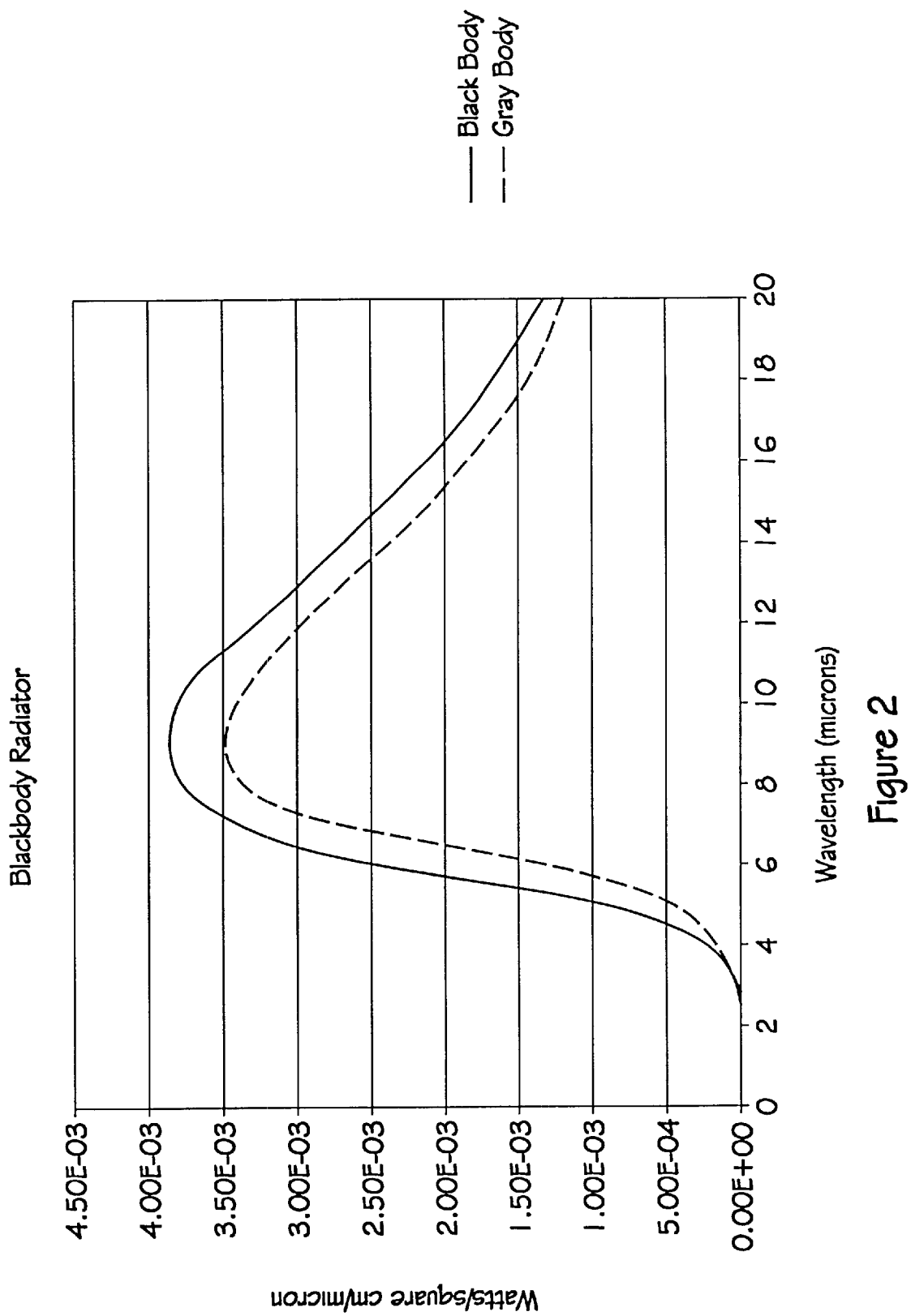
FIG. 2 is a graphical comparison of a true blackbody radiation spectrum with the emission spectrum of a human body, given in units of emitted energy at a given wavelength.

FIG. 1 shows the radiation distribution of a blackbody radiator ($e_m$=1) in comparison to a "graybody" radiator (e.g. human skin; $e_m$ of approximately 0.9). FIG. 2 shows the effect of temperature on spectral radiation emitted from the same body at increasing temperatures $T_0$, $T_1$, and $T_2$.

Figure 3:
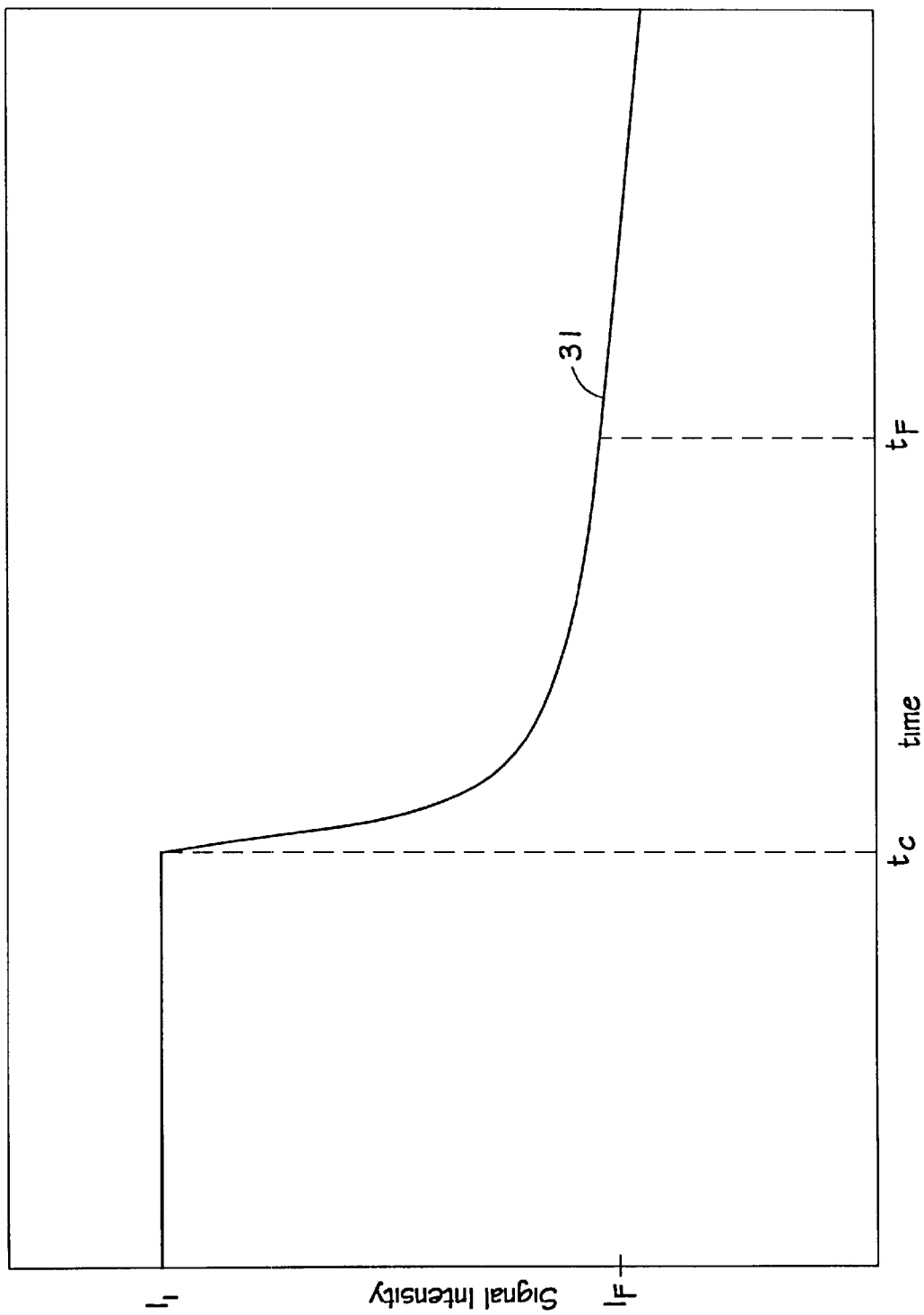
FIG. 3 is a graphical representation of detector signal response to an induced temperature gradient with the y-axis representing detector signal intensity and the x-axis representing time.

FIG. 3 graphically depicts a radiation detector output 31 of a typical sample monitored over time. Prior to inducing a temperature event, no gradient exists in the sample. Using a uniformly warm test sample at an initial temperature $T_i$, a detector signal 31 of constant intensity $I_i$ is measured. Without a temperature gradient, the signal 31 remains at a constant intensity $I_i$ By subjecting a sample to a temperature event, a temperature gradient is produced. To induce a gradient, the temperature event must be either cooler or warmer than the temperature $T_i$ of the sample. Either one works equally well. FIG. 3 illustrates the principle as applied to a cooling event. A cooling temperature $T_c$ is induced in the sample at a time $t_C$. Subsequently, the temperature of the sample begins to drop, resulting in a lower detector signal 31. At some later time $t_F$, the temperature reaches a new (and lower) equilibrium temperature, resulting in a lower detector signal 31 having intensity $I_F$. The opposite would be true if the sample was heated, resulting in a higher final equilibrium temperature and higher output signal intensity.

Another aspect of the surface cooling event is that, although the surface itself cools almost immediately due to its close physical proximity to the cooling event, the underlying regions, being further from the cooling source, cool somewhat more slowly. This phenomenon is schematically depicted in FIGS. 4(I)(a) through 4(IV)(b). FIG. 4(I)(a) depicts a typical sample material 40 prior to inducing a temperature event. The sample 40 depicted is at an arbitrarily warm uniform temperature $T_i$ (e.g., 30° C.). This means that the surface S of the sample 40 is at or about 30° C. and the interior d of the sample 40 is still at $T_i$ (about 30° C.) and no gradient is present. As shown in FIG. 4(I)(b), if no temperature event is induced in the sample 40, the temperature of the sample remains constant, no gradient exists, and a constant detector signal 31 is observed at an initial signal intensity.

Referring to FIGS. 4(I)(a) and 4(I)(b), if at some later time to the surface is subject to a cooling event (for example using a cooling event temperature $T_C$ of 10° C.), this situation begins to change. At first only the surface cools (shown as 10° C.), the rest of the sample remaining at an initial temperature $T_i$ (e.g. 30° C.). Just underneath the surface S, the sample begins to cool slightly from the initial temperature (30° C.). This results in a small temperature gradient G. This decline in temperature is accompanied by a decline in detector output signal 31 as shown in FIG. 4(I)(b).

Figure 4:
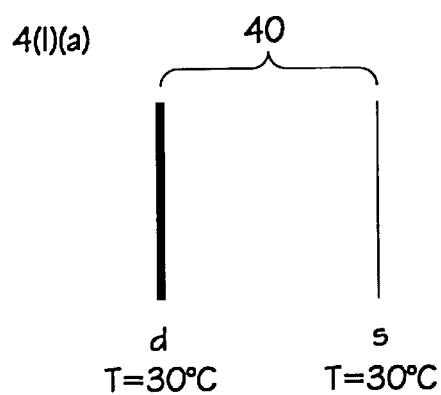
FIGS. 4(I)(a) through 4(IV)(b) are schematic diagrams showing the effect of a thermal gradient on radiation emitted from the skin's surface. The (a) series of Figures depict gradient effects in a physical test sample material. The (b) series of Figures are graphical depictions of the gradient effects as functions of detector signal and time.
Figure 4:
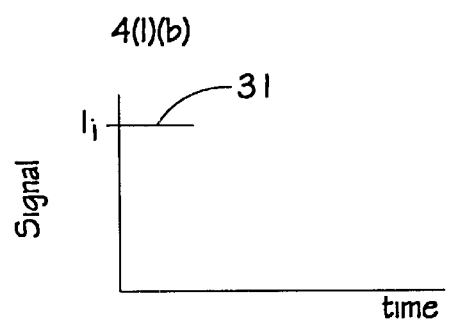
Figure 4:
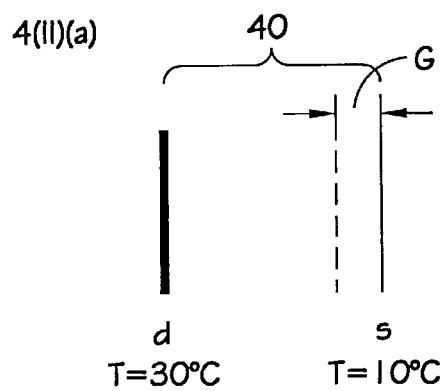
Figure 4:
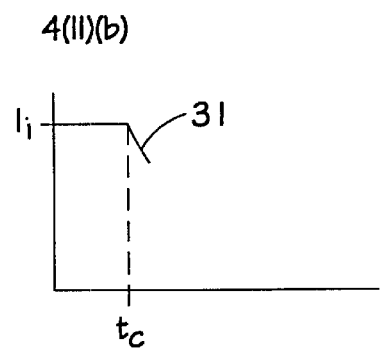
Figure 4:
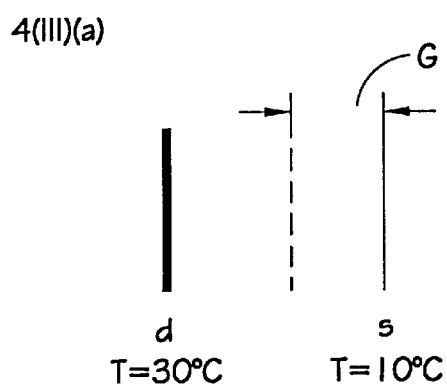
Figure 4:
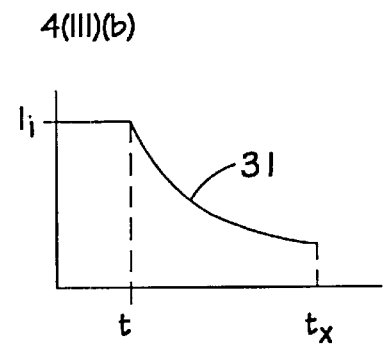
Figure 4:
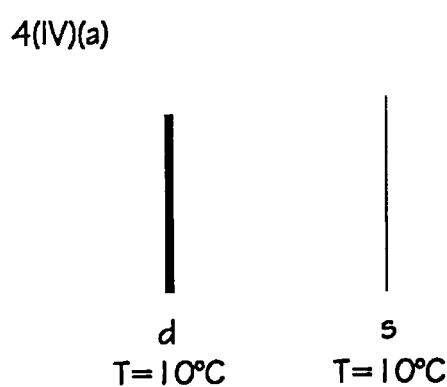
Figure 4:
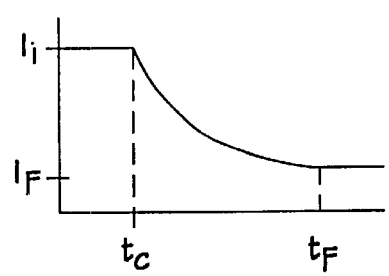

FIGS. 4(III)(a) and 4(III)(b) show the effects of the cooling event after some time $t_X$. Under the continued influence of the cooling event, the deeper regions of the sample continue to cool, enlarging the depth and magnitude of the gradient G. As the temperature of the sample 40 cools and the gradient increases, the detector signal 31 falls off, reflecting the effects of the declining temperature. As is obvious from the example above, the gradient effect is time dependent. Meaning, the longer the surface S is subjected to the cooling event, the colder the deeper regions of the sample will become. The lower limit on temperature being dictated by the temperature $T_C$ of the temperature event. Over time, the gradient G expands into the deeper regions of the sample 40. This creates a time-dependent temperature gradient in the sample.

Finally, as shown in FIGS. 4(IV)(a) and 4(IV)(b), the sample 40 reaches a new cooler steady state temperature (e.g. 10° C.) and the gradient G disappears. Consequently, the detected signal 31 from the sample 40 equilibrates at a new, lower, level $I_F$.

The time-varying nature of the temperature gradient may be exploited in a novel way to determine the concentration of various analytes contained in a test sample. By combining the effects of an induced temperature gradient with the principles of transmission cell spectroscopy, the present invention embodies an extremely accurate and non-invasive method of determining analyte concentration, which goes far beyond existing technologies.

Figure 5:
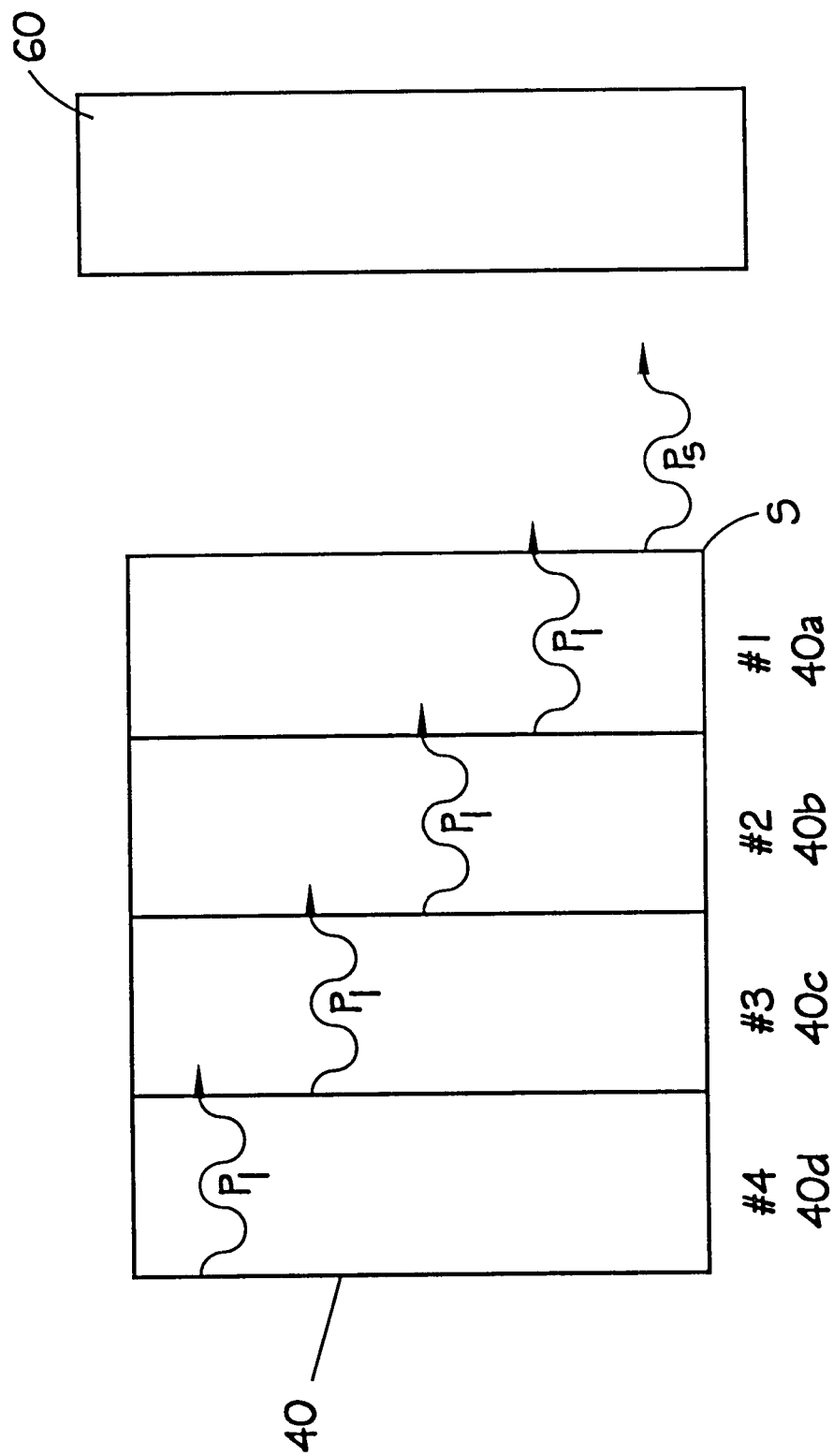
FIGS. 5 and 6 are the photon emission effects on cross-section views of a test sample in the presence and absence of a temperature gradient.
Figure 6:
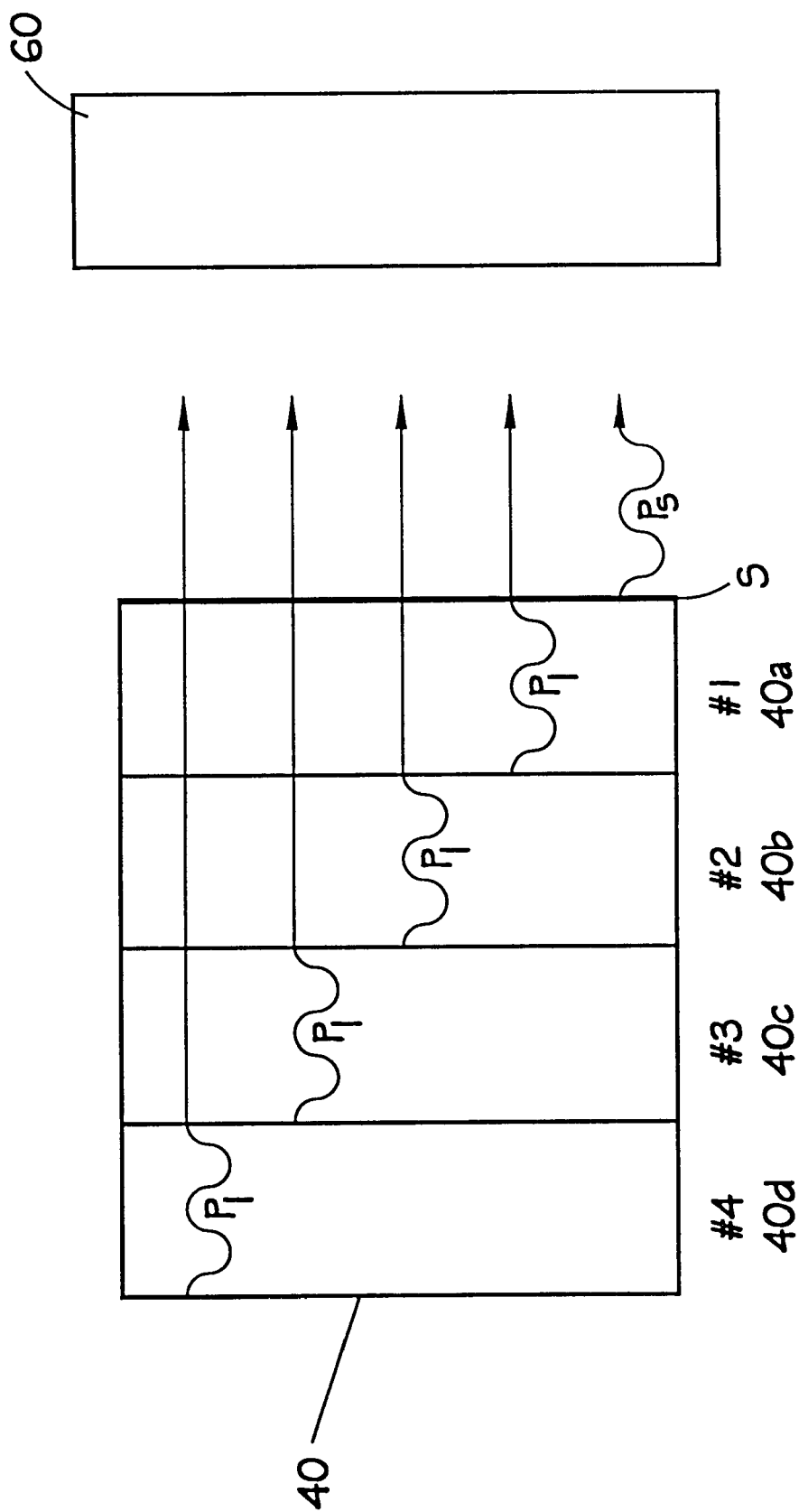

FIGS. 5 and 6 illustrate the transmission/absorbance aspect of the present invention. FIG. 5 is a cross-section view of a typical sample material 40 at an arbitrarily warm uniform temperature (e.g., about 37° C.). For illustrative purposes, the sample 40 of FIG. 5 is shown having a surface S and layers 40a, 40b, 40c, and 40d each representing successively deeper portions of the sample. Each layer being approximately 10 μm further inside the sample 40. Layer 40d being 30 μm beneath the sample surface S. Without a gradient, photons $P_d$ emitted within the sample are reabsorbed by the sample within a very short distance (approximately 10–20 μm). Only photons Ps emitted at or near the surface S exit the sample to be detected by an external detector 60. The radiation emission spectra of these photons $P_S$ is determined by the temperature and emissivity $e_m$ of the sample 40.

FIG. 6 shows the effects of inducing a gradient in the sample 40 of FIG. 5. The surface S has been cooled (e.g. to about 10° C.) while a deeper layer 40d remains warm (e.g. 37° C.) with the intervening layers 40a, 40b, 40c, exhibiting gradually cooler temperatures as the 10° C. surface S is approached. As previously explained, in the presence of a gradient, photons emitted from within the sample 40 travel much further before reabsorption by the sample 40. For example, an internal photon $P_1$ is emitted from the sample 40 from layer 40d and travels through layers 40a, 40b, 40c, and S. Since the photon $P_I$ is not reabsorbed by the sample 40, it can be detected by a radiation detector 60. Additionally, the internally emitted photons $P_I$ have a known characteristic radiation emission spectra based on the radiation emission characteristics of the sample material and temperature of the sample at the point at which the photon $P_I$ was emitted. Photons $P_I$ are detected and measured in concert with the photons $P_S$ emitted at or near the surface S, providing an overall radiation picture of the sample 40.

Referring to FIG. 6, the internally emitted photons $P_I$ pass through intervening sample material 40a, 40b, 40c, and S. The intervening material 40a, 40b, 40c, and S absorbs some of the radiation reducing radiation output by the time it reaches the detector 60. The analytes in the intervening regions 40a, 40b, 40c, and S absorb radiation at specific characteristic wavelengths. This reduces the radiation output at those wavelengths in a concentration-dependent manner. By comparing a detector signal at selected absorbance peak wavelengths with a reference signal at selected reference wavelengths, the analyte concentration may be determined.

Using this basic concept the present invention overcomes many of the practical impediments encountered in the prior art, including difficulties in resolving low analyte concentrations and tissue interference problems. The method of the present invention overcomes many of these difficulties by introducing a large temperature gradient in the sample to increase the detectable signal. Furthermore, by inducing a periodic temperature gradient in a sample substantial increases in accuracy and a much larger signal-to-noise ratio may be attained. The only limitations on gradient magnitude being the initial sample temperature and the necessity to avoid damaging the sample by making it too hot or too cold. These limitations become especially important when living tissue samples are used. Too high a temperature and the tissue burns, too cool and the tissue freezes. As a result preferable temperatures range from about 0° C. to about 40° C. for living test samples.

Description of Preferred Embodiments of the Invention

In its most basic embodiment the present invention provides a method for determining the concentration of chemical analytes in a test sample. The method is typically used in conjunction with a testing apparatus constructed for measuring analyte concentration. As shown in the block diagram of FIG. 7, such an apparatus 70 comprises a thermal gradient inducing means 62, a radiation detector 60, and a data processing means 64 for controlling the gradient and determining analyte concentration based on detector information and predetermined database. One satisfactory apparatus for implementing the method of the present invention is described in Attorney Docket No. P855, entitled "Solid-state Non-invasive Infrared Absorption Spectrometer for the Generation and Capture of Thermal Gradient Spectra from Living Tissue".

In the analysis of test samples the tester typically knows what analytes he is seeking. The analyte sought is identified, and its IR absorbance spectrum analyzed. Analyte absorbance peaks are identified. Once one or more absorbance peak wavelengths are identified, one or more reference wavelengths are chosen. A temperature gradient is induced in the test sample. Subsequently, the sample radiation emissions are monitored with an IR detector. Detector signals are monitored. Signals are monitored at predefined wavelength intervals defined by absorbance characteristics of the analyte sought. These signals are referred to as analytical emission signals or just analytical signals. Typically, the analytical signals are measured at analyte absorbance peak wavelengths. IR detector signals are also monitored at so-called reference wavelengths. These are referred to as reference emission signals or just reference signals. It is advantageous to measure reference signals at wavelengths do not overlap the analyte absorbance peaks and it is advantageous if reference signals and analytical signals are not measured at wavelengths that overlap absorbance peaks of other possible constituents of the sample.

The reference wavelengths are typically dictated by the absorbance spectrum of the main constituent of the sample. Commonly, the main constituent is the medium in which the analytes are suspended. Frequently, especially in biological samples, the main constituent is water. Therefore, any analyte measurement must take into consideration the large amounts of water present. Reference measurements may be taken in regions where sample media absorbance is low (i.e., transmission near 100%). However, there are advantages to using reference measurements taken in regions where the sample media absorbance is high (i.e., transmission near 0%). Alternatively, reference measurements may be taken in regions bracketing the analyte absorbance peaks in question. Ideally, analyte absorbance peaks are chosen in regions where the absorbance effects of the major constituents are small. It is the way in which the information gathered at these absorbance and reference wavelengths is processed which allows the present invention to determine analyte concentration.

The present invention combines detector output measurements taken at the appropriate wavelengths with analysis of the radiation emission spectra of the subject material at known temperatures to facilitate the accurate determination of analyte concentration.

As previously discussed, most analytical samples exhibit blackbody or near blackbody radiative characteristics. This allows an accurate prediction of the expected radiation emission spectra based on temperature. Deviations from this expected spectra at selected wavelengths provide information used to determine analyte concentration.

A. Embodiment of the Present Invention Using a Non-Periodic Gradient

An application of the present invention is illustrated in the following non-invasive determination of blood ethanol concentration in a human test subject.

Figure 9:
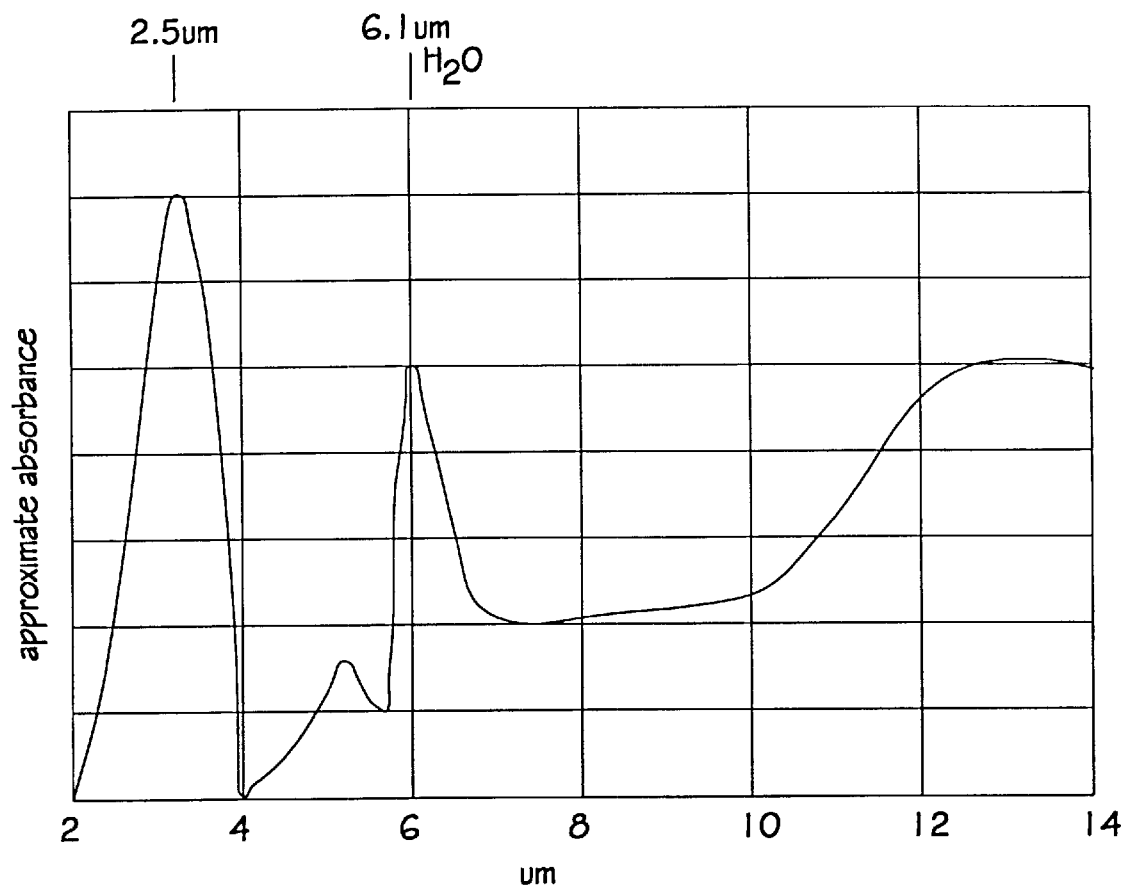
FIGS. 9, 10, and 11 show the absorbance spectra of water, ethanol, and glucose, respectively.
Figure 10:
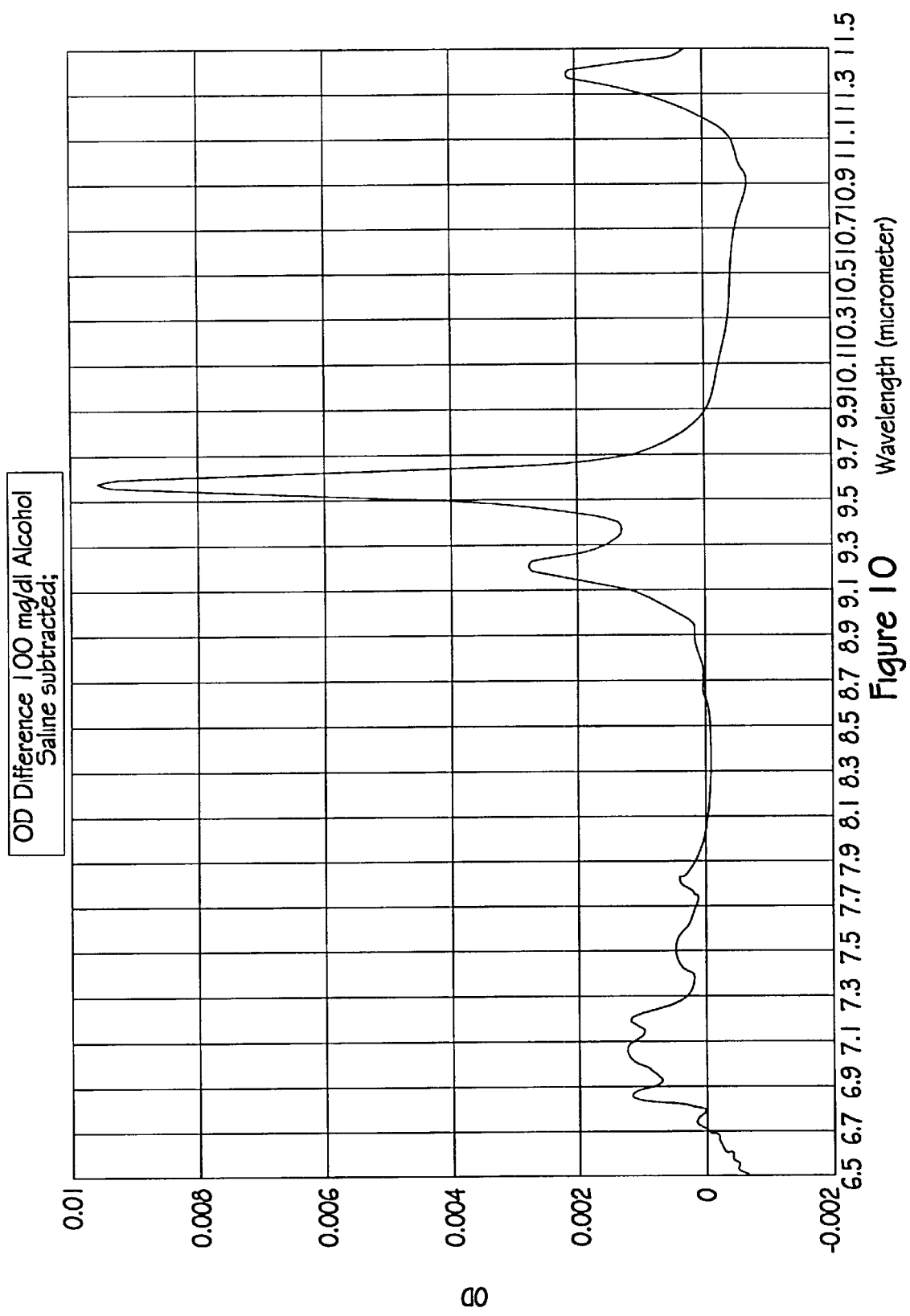

The major constituent of human blood is water. Blood is essentially a suspension of biological compounds in a water media. For the purpose of this illustration, the analyte of interest is ethanol. FIGS. 9 and 10 depict the IR spectra of water and glucose, respectively. Referring to FIG. 9, water absorbance peaks are present at 2.9 $\mu$m and 6.1 $\mu$m. A transmittance peak exists in the range of about 3.6 cm to 4.2 cm. Additionally an area of relatively uniform absorbance exists between about 6.8 $\mu$m and about 11.0 $\mu$m. Referring to FIG. 10, ethanol absorbance peaks are shown between about 9.3 $\mu$m and 10.1 $\mu$m.

For the sake of illustration, we assume that the sample (blood and ethanol) has an mission spectrum similar to a blackbody radiator (FIG. 2). The blackbody radiative characteristics provide a source of known IR radiation which may be used to analyze the constituents of the sample.

Figure 7:
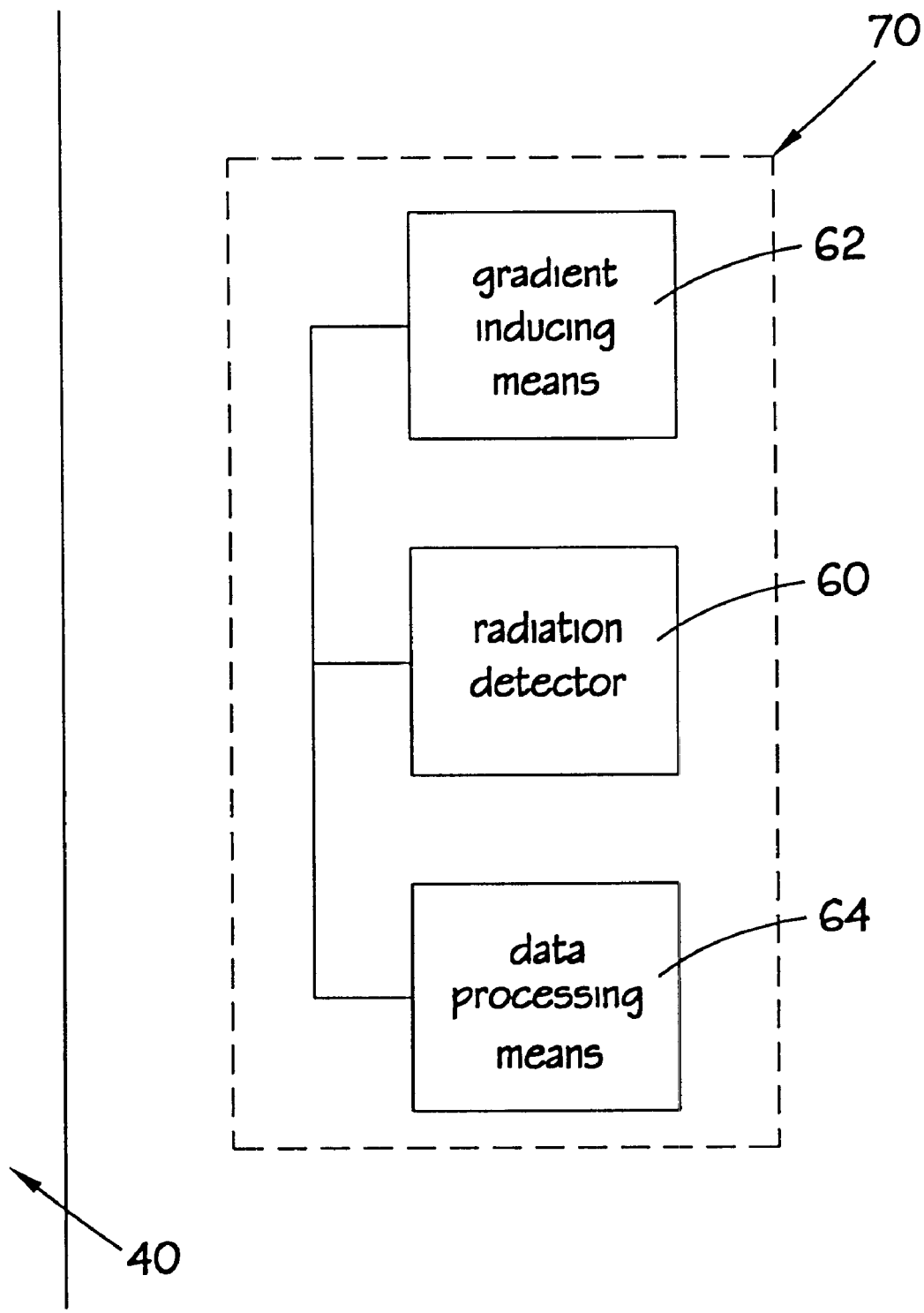
FIG. 7 is a block diagram showing a satisfactory apparatus for implementing the method of the present invention.
Figure 8:
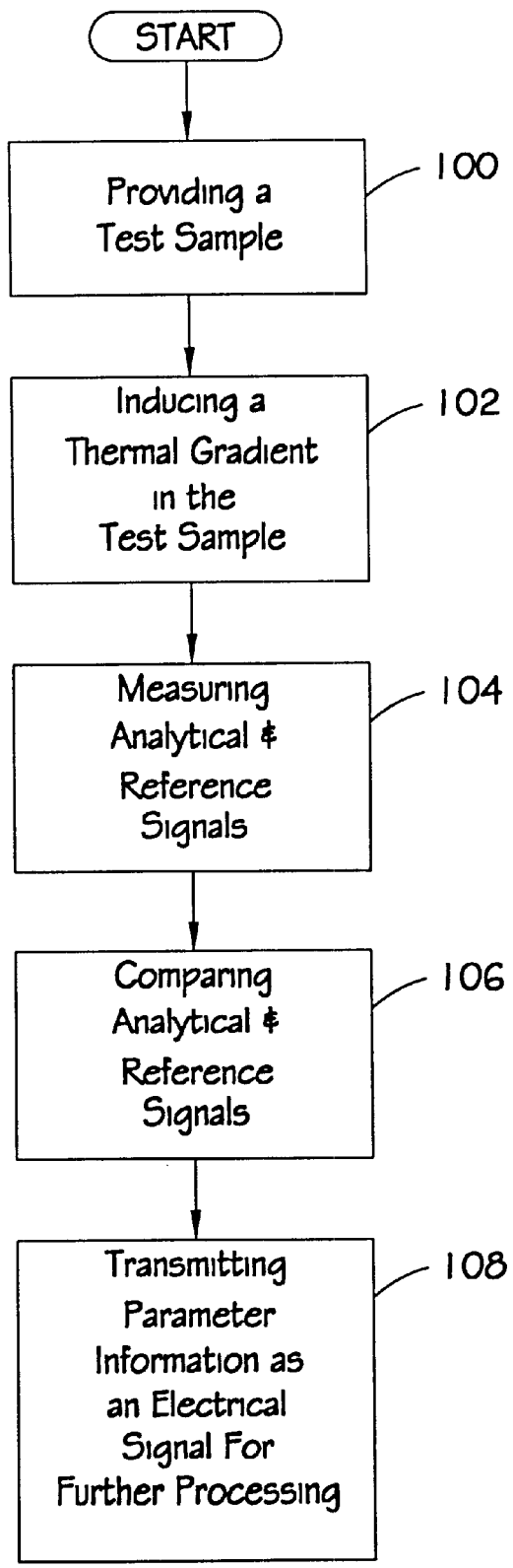
FIG. 8 is a flowchart showing an embodiment of the present invention.

Referring to FIGS. 7 and 8 an apparatus of FIG. 7 is employed according to the flowchart of FIG. 8. In Step 100 a test sample 40 is provided at some arbitrarily warm constant uniform initial temperature (e.g., approximately 37° C.), no gradient exists. In Step 102, a temperature gradient is induced in the sample 40 (for example, by subjecting the surface of the sample to a cooling event using means 62). Radiation passing through the gradient passes through the ethanol suspended in the sample and reaches the surface where it is detected by an IR detector 60. In Step 104 radiation is measured at selected wavelengths (specifically, at reference wavelengths and analyte absorbance peaks) producing analytical signals and reference signals. In Step 106 analytical signals and reference signals are compared and analyzed to determine phase differences caused by changes in the absorbance spectra in the affected regions. The present invention determines the analyte concentration in the sample by comparing the absorbance effects of the analyte with known absorbance information. This comparison and analysis is typically done using a data processing means 64. In Step 108, this concentration information is then transmitted, as an electrical signal, for further processing.

Figure 12:
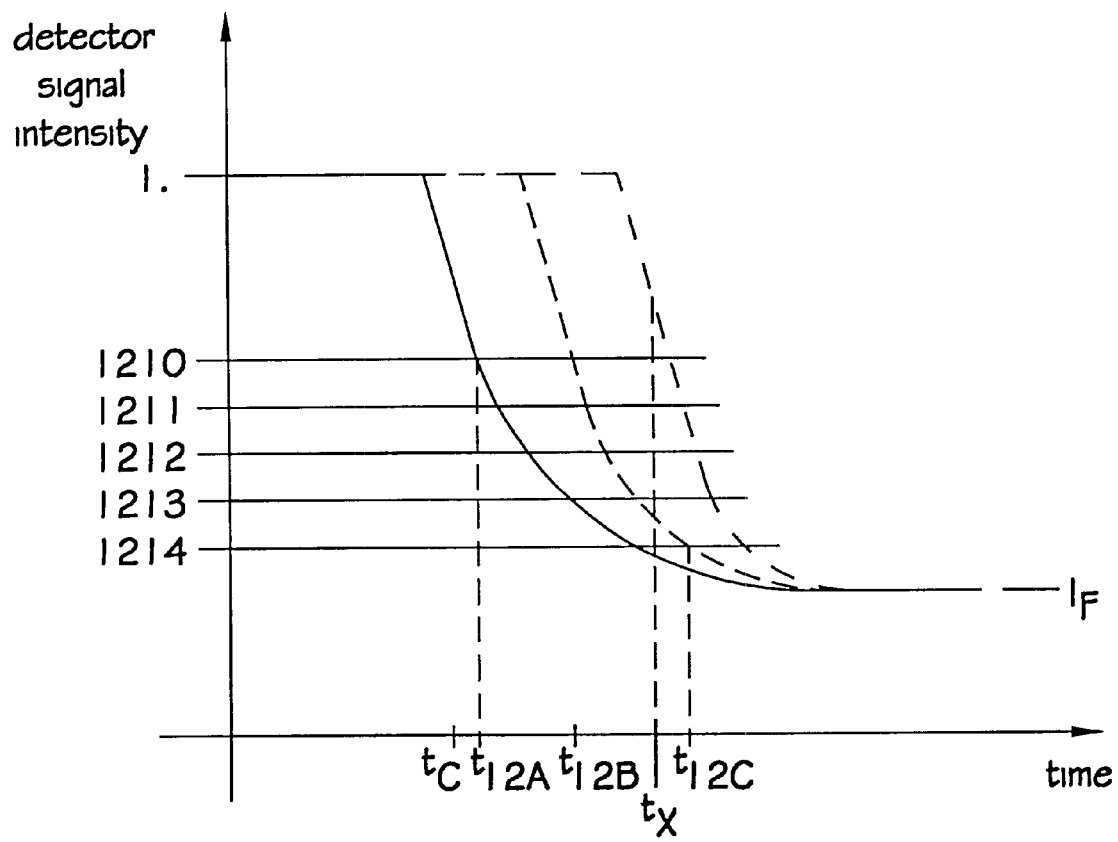
FIG. 12 is a graphical representation of the skin's response to a single induced temperature gradient with the y-axis representing detector signal intensity and the x-axis representing time.

Referring to FIGS. 8 and 12, in Step 104, a first reference signal 12A may be measured at a first reference wavelength. In the case of ethanol in a water media, a first reference signal is measured at a wavelength where water strongly absorbs (e.g., 2.9 $\mu$m or 6.1 $\mu$m as shown in FIG. 9). Because water strongly absorbs radiation at these wavelengths, the detector signal intensity is reduced at those wavelengths. Moreover, at these wavelengths water absorbs the photon emissions emanating from deep inside the sample. The net effect being that a signal emitted from deep inside the sample is not detected. The first reference signal 12A is a good indicator of gradient effects near the, sample surface and is known as a surface reference signal. This signal may be calibrated and normalized to a value of 1. For greater accuracy, the detector signal at more than one first reference wavelength may be measured. For example, both 2.9 $\mu$m and 6.1 $\mu$m may be chosen as first reference wavelengths.

Still referring to FIG. 12, a second reference signal 12C may also be measured. The second signal 12C may be measured at a wavelength where water has very low absorbance (e.g., 3.8 $\mu$m or 5.5 $\mu$m as shown in FIG. 7). Unlike the first reference signal 12A, the second reference signal 12C is measured at a wavelength largely transparent to radiation. This signal may also be calibrated and normalized to a value of 1. This second reference signal 12C provides the analyst with information concerning the deeper regions of the sample, whereas the first signal 12A provides information concerning the sample surface. As with the first (surface) reference signal 12A, greater accuracy may be obtained by using more than one second (deep) reference signal 12C.

In order to determine analyte concentration, a third signal 12B is also measured. This signal is measured at an IR absorbance peak of the selected analyte. Ethanol peak wavelengths are in the range of about 9.3–10.1 $\mu$m (as shown in FIG. 9). This detector signal may also be calibrated and normalized to 1. As with the reference signals 12A, 12C, the analytical signal 12B may be measured using more than one absorbance peak.

Optionally, or additionally, reference signals may be measured at wavelengths that bracket the analyte absorbance peak. Using the ethanol example, bracketing wavelengths may be chosen at 7.0–8.0 $\mu$m and 10.3–11.5 $\mu$m. These signals may also be calibrated and normalized to a value of 1. These signals may be advantageously monitored at reference wavelengths which do not overlap the analyte absorbance peaks. Further, it is advantageous to measure reference wavelengths and absorbance peaks which do not overlap the absorbance peaks of other possible constituents contained in the tissue. Corrections for known extraneous biological matter contained in a sample may be made if desired.

In Step 106, the analytical 12B and reference signals 12A, 12C are compared.

Referring to FIG. 12, the signal intensities 12A, 12B, 12C all begin at an initial signal intensity (all shown here at a normalized value of 1). This reflects the baseline radiation behavior of a test sample in the absence of a gradient. In Step 102, at some time, $t_C$, the surface of the sample is subjected to a temperature event which induces a temperature gradient in the sample surface. This gradient can be induced by heating or cooling the sample surface. The example shown in FIG. 12 uses cooling, for example, using a 10° C. cooling event. Similar to FIG. 3, the detector signal decreases over time. However, due to the effects of the temperature gradient and variances in absorbance, each signal 12A, 12B, 12C decreases in intensity.

Since the cooling of the sample is neither uniform nor instantaneous, the surface cools before the deeper regions of the sample cool. As each of the signals 12A, 12B, 12C are monitored as they drop in intensity, a pattern emerges. Signal intensity declines as expected, but if the signals are monitored as they reach a set amplitude value (or series of amplitude values: 1210, 1211, 1212, 1213, 1214), certain temporal effects are noted. After the cooling event is induced at $t_C$, the first (surface) reference signal 12A declines in amplitude most rapidly, reaching a checkpoint 1210 first, at time $t_{12A}$. This is due to the fact that the first reference signal 12A mirrors the sample's radiative characteristics near the surface of the sample. Since the sample surface cools before the underlying regions, the surface (first) reference signal 12A drops in signal intensity first.

Simultaneously, the second reference signal 12C is monitored. Since the second reference signal 12C mirrors the radiation characteristics of deeper regions inside the sample, which do not cool as rapidly as the surface (due to the time needed for the surface cooling to propagate into the deeper regions of the sample), the intensity of signal 12C does not decline until slightly later. Consequently, signal 12C does not reach magnitude 1210 until some later time $t_{12C}$. This results in a time delay between the time $t_{12A}$ that the amplitude of the first reference signal 12A reaches the checkpoint 1210 and the time $t_{12C}$ that the second reference signal 12C reaches the same checkpoint 1210. This time delay can be expressed as a phase difference $\emptyset(\lambda)$. Additionally, a phase difference may be measured between the analytical signal 12B and either or both reference signal 12A, 12C. These phase differences $\emptyset(\lambda)$ are compared in Step 106 of FIG. 8. As the concentration of analyte increases, the amount of absorbance at the analytical wavelength increases. This reduces the intensity of the analytical signal 12B in a concentration dependent way. Consequently, the analytical signal 12B reaches intensity 1210 at some intermediate time $t_{12B}$. The higher the concentration of analyte, the more the analytical signal 12B shifts to the left. As a result, with increasing analyte concentration, the phase difference $\emptyset(\lambda)$ relative to the first reference signal 12A decreases and relative to the second reference signal 12C (the deep. tissue signal) the phase difference $\emptyset(\lambda)$ increases. These phase differences $\emptyset(\lambda)$ are directly related to analyte concentration and can be used to make accurate determinations of analyte concentration.

Phase difference $\emptyset(\lambda)$ between the surface reference signal 12A and the analytical signal 12B is represented by the equation:

$$\emptyset(\lambda)=|t_{12A}-t_{12B}|$$

The magnitude of this phase difference decreases with increasing analyte concentration.

Whereas, the difference $\emptyset(\lambda)$ between the deep 12C and analytical 12B signals is represented by the equation:

$$\emptyset(\lambda)=|t_{12B}-t_{12C}|$$

The magnitude of this phase difference increases with increasing analyte concentration.

Accuracy may be enhanced by choosing several checkpoints, for example, 1210, 1211, 1212, 1213, and 1214 and averaging the phase difference $\emptyset(\lambda)$. The accuracy of this method may be further enhanced by integrating the phase difference $\emptyset(\lambda)$ continuously over the entire test period. Because only a single temperature event has been induced and because measurements must be taken only in the presence of a temperature gradient all measurements must be taken before a new lower equilibrium temperature is reached and the signals stabilize at a new constant level $I_F$ and the gradient vanishes. Further accuracy may be obtained by measuring detector signals at reference wavelengths chosen near analyte absorbance peaks. The point should be made that the method works equally well with temperature gradients induced by heating.

Furthermore, the method of the present invention is not limited to the determination of phase difference $\emptyset(\lambda)$. At any given time (for example, at time $t_x$) the amplitude of the analytical signal 12B may be compared to the amplitude of either or both of the reference signals 12A, 12C. The difference in signal magnitude may be correlated and processed to determine analyte concentration. Also, the analytical signal 12B and the reference signals 12A, 12C may be processed for concentration dependent frequency information. The differences in each of these parameters (phase, magnitude, and frequency) may be processed using the data processing means of the present invention (not shown) to determine analyte concentration.

The invention is versatile, this method is not limited to the detection or quantification of in-vitro ethanol concentration. As stated previously, the method may be used on human, animal, or even plant subjects. The method may be used to take non-invasive measurements of in-vivo samples of virtually any kind. In addition to blood samples, the method is adaptable and may be used to determine chemical concentrations in other body fluids (e.g., urine or saliva) once they have been extracted from a patient. In fact, the method may be used for the measurement of in-vitro samples of virtually any kind. The method is useful for measuring the concentration of a wide range of additional chemical analytes, including but not limited to, glucose, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, hormones, as well as other chemical compounds. All that is required is the careful selection of analytical and reference wavelengths.

B. Embodiment of the Present Invention Using Periodically Modulated Temperature Gradients The principles of the present invention may be applied to a more elegant method of determining analyte concentration. By using a periodically modulated temperature gradient, a more accurate determination of analyte concentration may be made.

Figure 13:
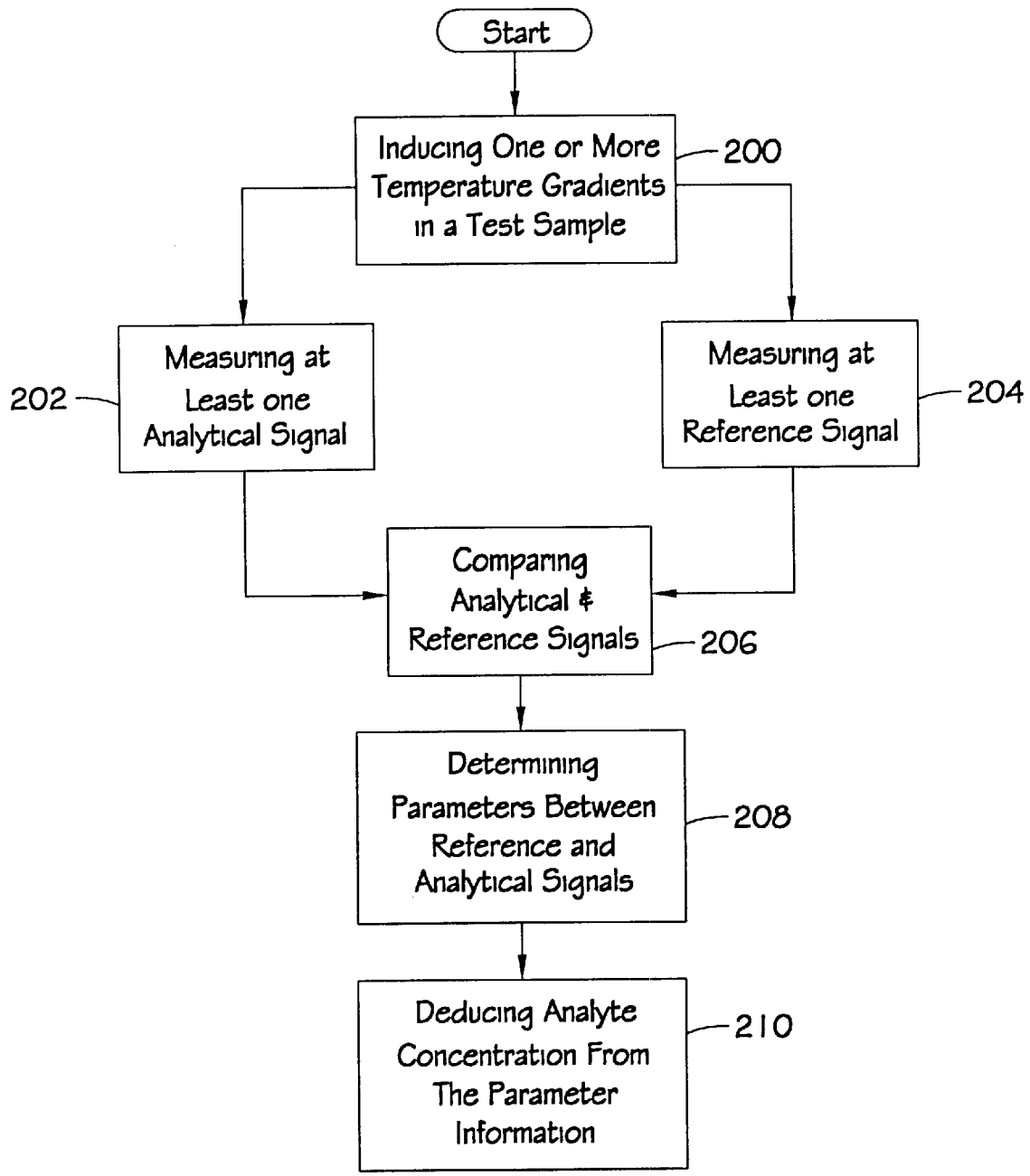
FIG. 13 is a flowchart showing a second embodiment of the present invention.

FIG. 13 is a flowchart of an embodiment of the present invention using a periodically modulated temperature gradient to determine the analyte concentration of a sample. In Step 200, a periodic gradient is induced in a sample. In Steps 202 and 204, the radiation output of the sample is measured using at least one analytical signal and at least on reference signal. In Step 206 the analytical and reference signals are compared and processed. Subsequently, in Step 208, the processed information is used to determine parameter differences between said analytical and reference signals. In Step 210, the parameter signal is used in conjunction with predetermined parameter information to deduce the analyte concentration of the sample.

Figure 11:
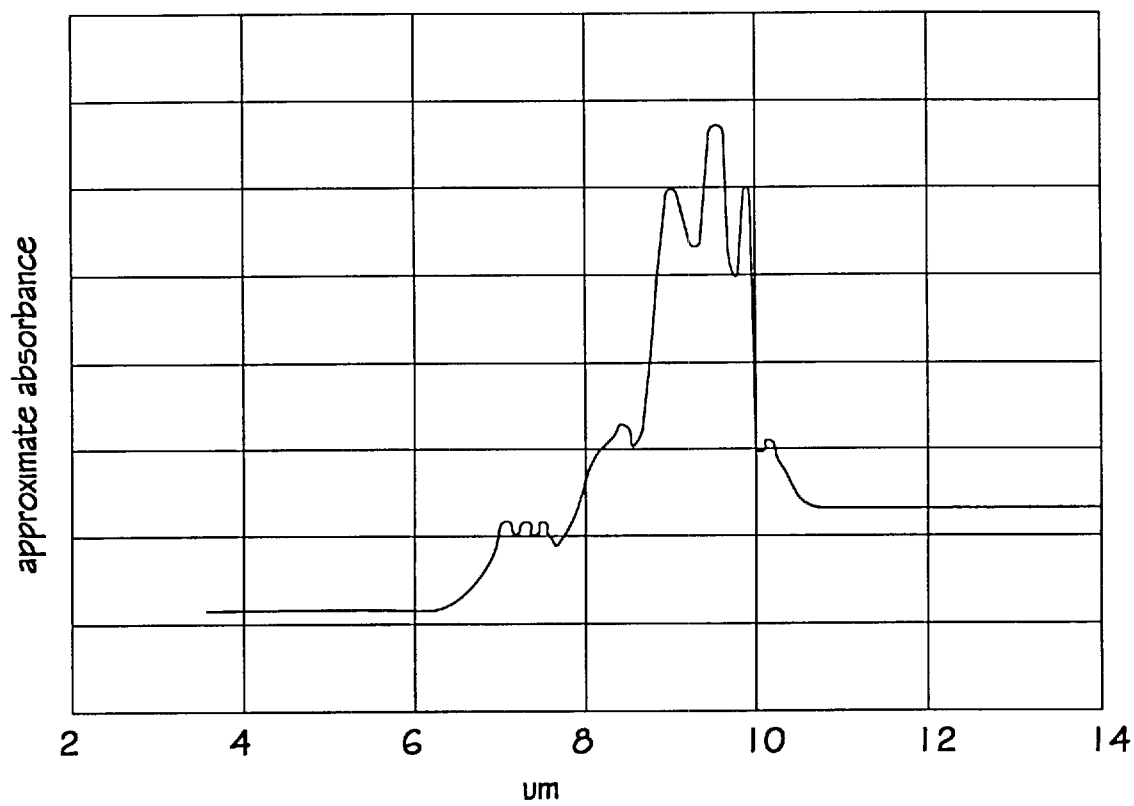

The following example illustrates a determination of blood glucose concentration in a test sample. The parameter chosen in this example is phase difference (but may also be frequency or amplitude). FIGS. 9 and 11 depict the IR spectra of water and glucose, respectively. Referring to FIG. 9, water absorbance peaks are present at 2.9 µm and 6.1 µm.

A transmittance peak exists in the range of about 3.6 μm to 4.2 μm. Additionally, an area of relatively uniform absorbance exists between about 6.8 μm and about 11.0 μm. Referring to FIG. 11, a number of glucose absorbance peaks exist between about 6.5 μm and 11.0 μm.

As previously shown, in FIG. 12, once a gradient is induced, the reference and analytical signals 12A, 12B, 12C are out of phase with respect to each other. This phase difference Ø(λ) is present whether the gradient is induced through heating or cooling. This feature of the invention has tremendous advantages. The present invention advantageously exploits the fact that phase difference Ø(λ) exists in the presence of both positive and negative gradients. By alternatively subjecting the test sample to cyclic pattern of heating then cooling, a continuous gradient may be induced in a sample for an extended period of time.

Figure 14:
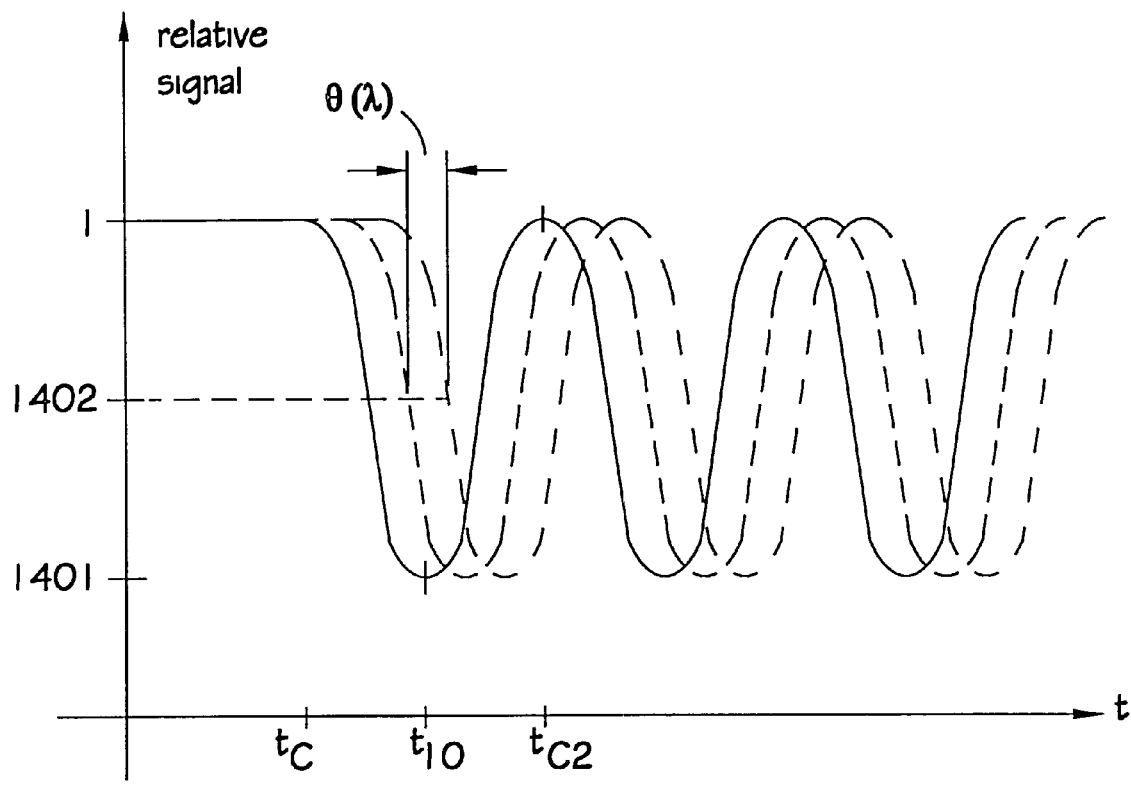
FIG. 14 is a graphical representation of skin response to a periodically modulated temperature gradient with the y-axis representing detector signal intensity and the x-axis representing time.

The principle of a continuous gradient is illustrated using a simple sinusoidally modulated temperature gradient. FIG. 14 graphically depicts detector signals emanating from a test sample. As with the previously disclosed embodiment shown in FIG. 12, one or more reference signals 14A, 14C are measured. One or more analytical signals 14B are also monitored. These signals may optionally be normalized to a value of 1. FIG. 14 shows the signals after normalization. At some time to, a temperature event (e.g., cooling) is induced at the sample surface. This causes a decline in detector signal. As shown in FIG. 12, the signals (12A, 12B, 12C) decline until the gradient disappears and a new equilibrium detector signal $I_F$ is reached. In the present embodiment (FIG. 14), as the gradient begins to disappear at signal intensity 1401 a heating event, at time $t_W$, is induced in the sample surface. As a result the detector output signals 14A, 14B, 14C will rise as the sample temperature rises. At some later time $t_{C2}$, another cooling event is induced, causing the temperature and detector signals to decline. This cycle of cooling and heating may be repeated over an arbitrarily long time interval. Moreover, if the cooling and rewarming events are timed properly, a periodically modulated temperature gradient may be induced in the test sample. Such a periodic gradient is the objective of Step 200 of FIG. 13.

As previously explained in the discussions relating to FIG. 12, a phase difference Ø(λ) may be measured and used to determine analyte concentration. In the present embodiment, periodic reference (14A, 14C) and analytical 14B signals are measured in Steps 202 and 204. The reference (14A, 14C) and analytical 14B wavelengths are chosen for analysis based on the same considerations used to determine the reference and analytical wavelengths shown in FIG. 12 (i.e., absorbance peaks, transmission peaks, non-interference with the media). FIG. 14 shows these signals after an optional normalization step has occurred.

FIG. 14 shows that a first (surface) reference signal 14A declines and rises in intensity first. A second (deep tissue) reference signal 14C declines and rises in a time-delayed manner relative to the first reference signal 14A. The analytical signal 14B exhibits a time delay dependent on the analyte concentration. With increasing concentration, the analytical signal 14B shifts to the left. As with FIG. 12 a phase difference Ø(λ) may be measured.

In Steps 206 and 208, reference signals 14A, 14C are compared with analytical signals 14B to determine a phase difference Ø(λ). For example, a phase difference Ø(λ) between the second reference signal 14C and an analytical signal 14B, measured at some set amplitude 1402 is shown. The phase difference Ø(λ) can be used to determine the phase difference between any reference signal 14A, 14C and any analytical signal 14B to generate a phase signal as in Step 208. The magnitude of the phase signal reflects the analyte concentration of the sample. In Step 210 the phase difference Ø(λ) information is correlated by the data processing means 64 with previously determined phase information (typically stored in the data processing means 64 of FIG. 7) to determine the analyte concentration in the sample.

A further advantage of the present method is that the phase difference Ø(λ) is constant and continuous measurements of phase may be integrated over the entire test period for an extremely accurate measure of phase difference Ø(λ). By inducing and maintaining a temperature gradient and integrating continuous measurements of phase difference Ø(λ) throughout an entire test period, the signal-to-noise ratio may be substantially increased resulting in very accurate determinations of phase. Further, the accuracy of the method may be improved by using more than one reference signal and/or more than one analytical signal.

Additionally, the present method may be advantageously employed to simultaneously measure the concentration of one or more analytes. By choosing reference and analyte wavelengths that do not overlap, phase differences can be simultaneously measured and processed to determine analyte concentrations.

Although FIG. 14 illustrates the method used in conjunction with a sinusoidally modulated temperature gradient, the principle applies to temperature gradients conforming to any periodic function. In such more complex cases, analysis using signal processing with Fourier transforms or other techniques allows accurate determinations of phase difference Ø(λ) and analyte concentration. Such processing may be accomplished using the data processing means 64 of FIG. 7.

Figure 15:
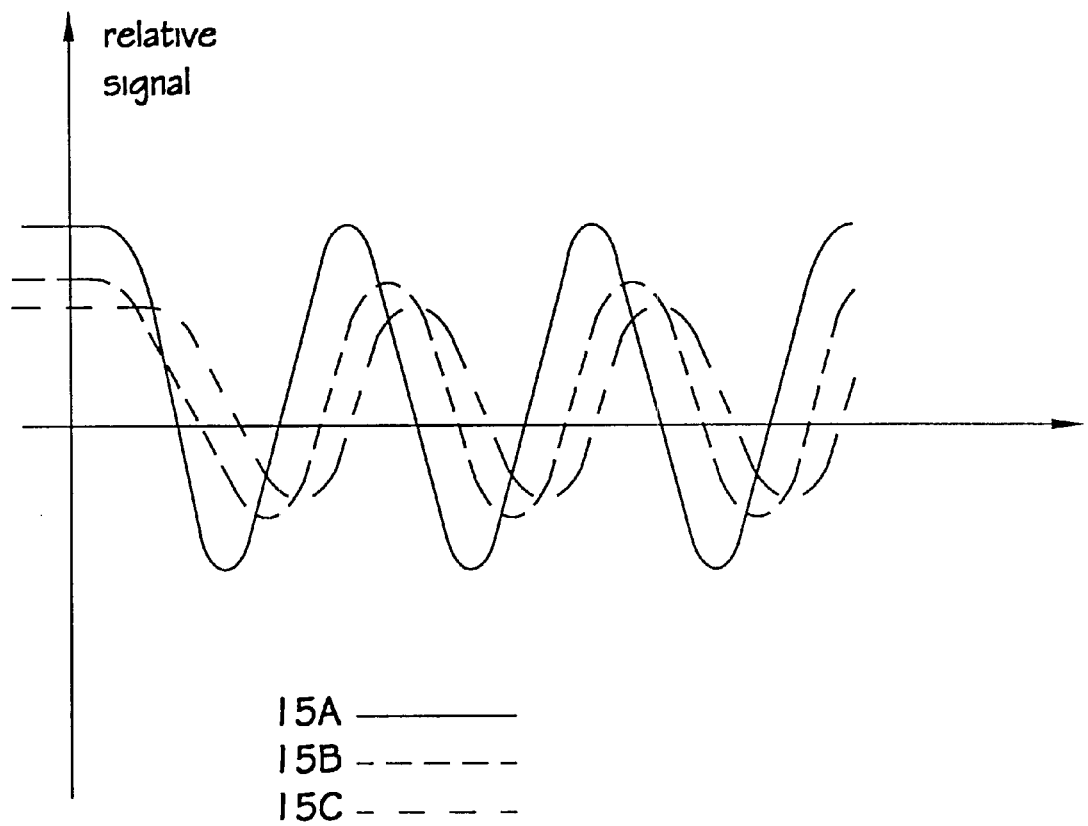
FIG. 15 is a graphical representation of skin response to a periodically modulated temperature gradient with the y-axis representing unnormalized detector signal intensity and the x-axis representing time.

C. Embodiment of the Present Invention Using Periodic Monitoring of Phase Signal Referring to FIG. 15, further advantages of the present invention include the ability to accurately determine analyte concentration using non-continuous measurements of phase. For example, the magnitude of the phase differences Ø(λ) may be determined by measuring the time intervals between the amplitude peaks (or troughs) of the reference signals 15A, 15C and the analytical signals 15B. Alternatively, the time intervals between the "zero crossings" (the point at which the signal amplitude changes from positive to negative, or negative to positive) may be used to determine the phase difference Ø(λ) between analytical signals 15B and the reference signals 15A, 15C. This information is subsequently processed and a determination of analyte concentration may then be made. The method has the advantage of not requiring normalized signals.

D. Embodiment of the Present Invention Using Periodic Gradients Induced at More Than One Driving Frequency Additionally, this application of the principles of the invention allows non-invasive quantification of analyte concentration in test samples comprised of heterogeneous material, such as complex biological tissues. A typical example being human skin.

Figure 16:
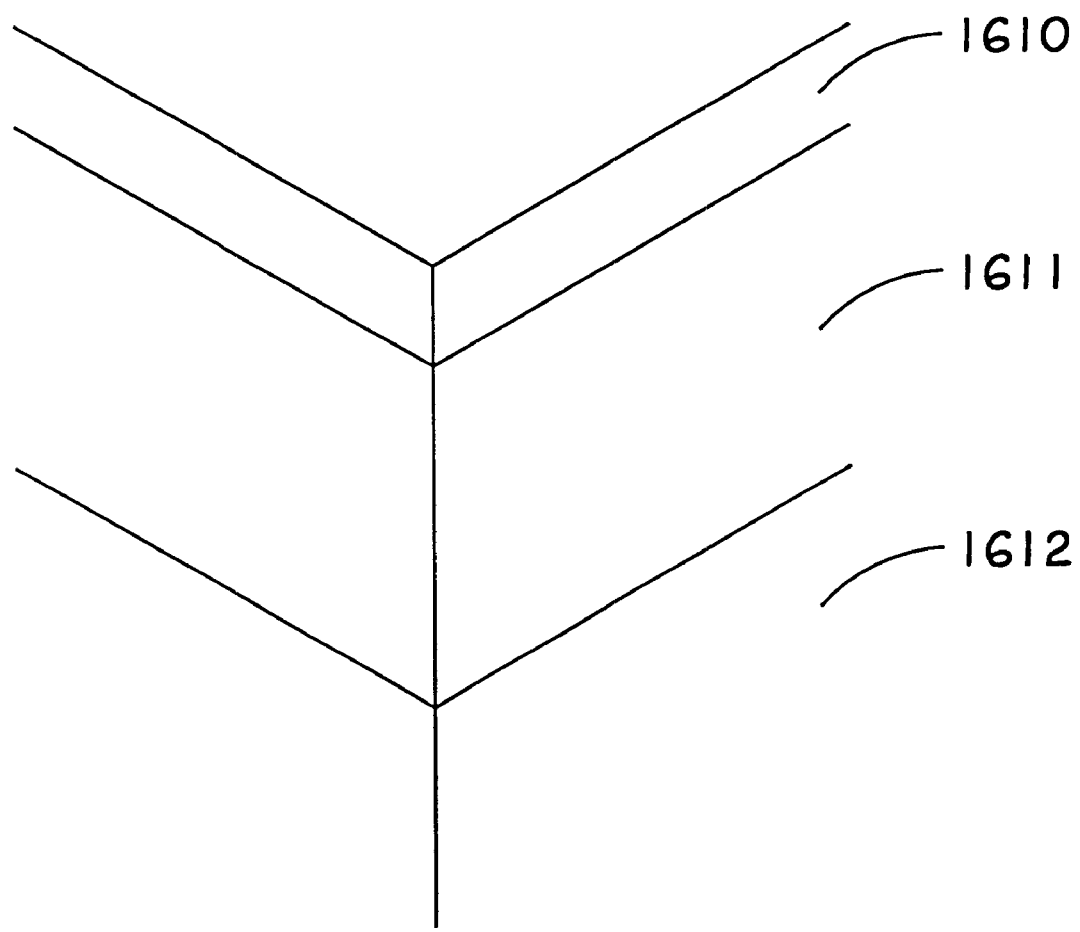
FIG. 16 is a schematic illustration of the human skin.

The skin's structure differs from the completely uniform homogeneous examples previously described. As shown in FIG. 16, skin is a layered structure. A thin layer of stratum corneum approximately 10 μm thick 1610 covers the surface of the skin, and contains no fluid. Underlying the stratum corneum is a layer of epidermis 1611 approximately 100 μm thick. The epidermis 1611 contains fluids (e.g., interstitial and intracellular fluids) which are important because the fluids suspend analyte materials of interest (such as glucose). Beneath the epidermis 1611 lies a thick layer of derma 1612, which also contains fluid and suspended blood analytes (for example, glucose). It is the methods for analyzing these suspended analytes that form the present embodiment of the invention.

The human body's spectral radiation characteristics are very similar to that of the previously discussed blackbody radiator (FIG. 2). The near blackbody radiative characteristics of the human body provide a source of known IR radiation, which may be used to analyze the constituents of human blood contained within the skin.

Ordinarily, the body's internal temperature $T_I$ is constant at approximately 37° C. At ordinary room temperature (e.g., 21° C.), a naturally occurring temperature gradient exists in the skin. A 21° C. room temperature is less than the body's 37° C. internal temperature $T_I$. This causes a reduction of the skin's surface temperature $T_S$ to approximately 33° C. As a consequence, a small 4° C. temperature gradient exists between the body's 37° C. internal regions and the skin's 33° C. surface. Unfortunately, this naturally occurring gradient is not sufficient and a larger gradient is needed. The larger gradient equates to a greater detector signal and a better picture of thermal behavior deeper inside the skin. The present invention utilizes this phenomenon to analyze the body's chemical composition.

The present invention integrates all the previous concepts in a method of determining analyte concentration in heterogeneous (non-uniform) test samples. Specifically, the method of the present invention may be used to non-invasively determine the blood glucose concentration in human subjects. It allows the measurement of specific regions inside a test sample. This has significant advantages when used to analyze samples having non-uniform analyte distribution characteristics. This method finds particular utility in the non-invasive analysis of biological tissues.

It will be recalled from the discussions concerning FIGS. 4(I)(a) through 4(IV)(b) that the temperature gradient penetrates into a test sample on a time-dependent basis (i.e., the longer the surface temperature event was present, the deeper the gradient penetrated into the sample). It is also recalled that photons emitted from areas beneath the gradient are reabsorbed within 10–20 μm of their point of origin, meaning that photons emanating from beneath the gradient do not reach the surface and are not detected. This allows the present invention to examine "slices" of a test sample at various depths.

Figure 17:
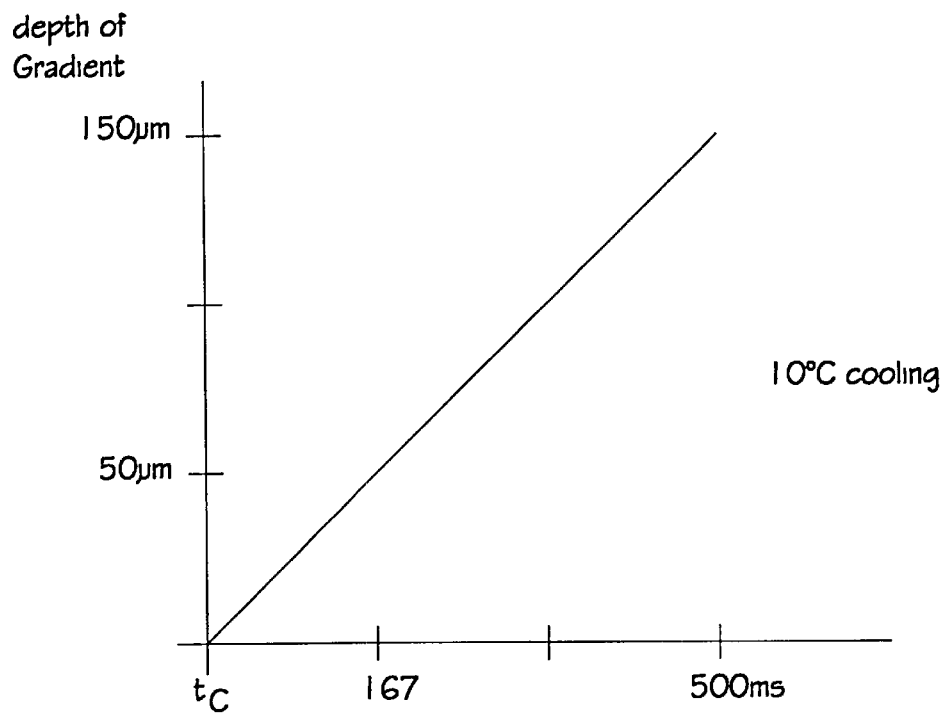
FIG. 17 is a graphical representation of skin response to a periodically modulated temperature gradient with the y-axis representing the depth to which the gradient penetrates and the x-axis representing the time that the skin has been exposed to a 10° C. cooling source.
Figure 18:
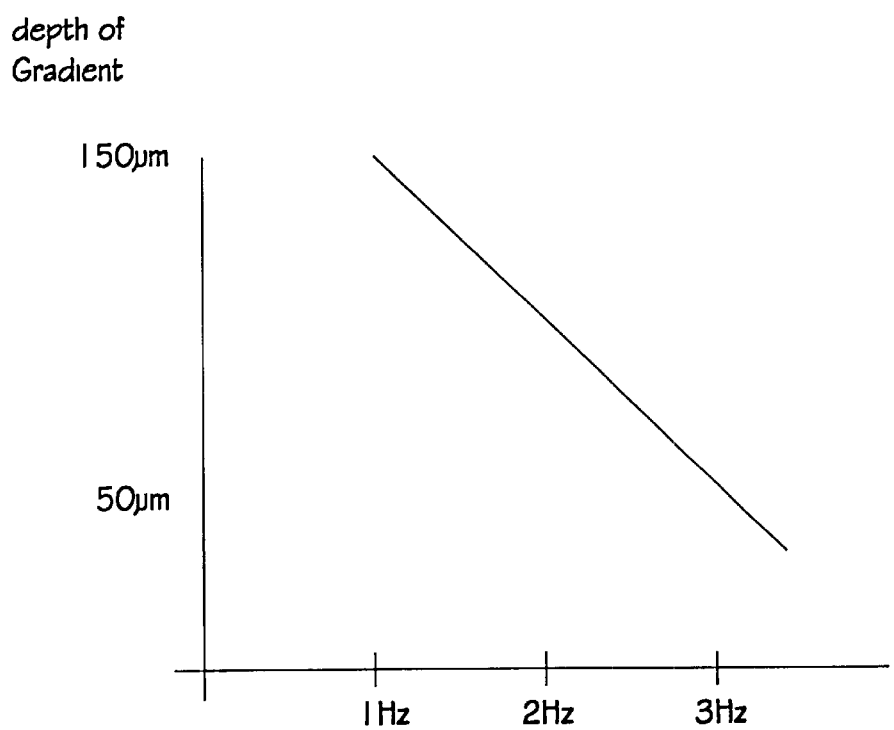
FIG. 18 is a graphical representation of skin response to a periodically modulated temperature gradient with the y-axis representing the depth to which the gradient penetrates and the x-axis representing the frequency of a gradient cooling/heating cycle.

FIGS. 17 and 18 illustrate this principle. FIG. 17 plots length of a temperature event versus depth of gradient. FIG. 18 plots frequency of a periodic cooling/heating cycle versus depth of gradient. Referring to FIG. 3, initially a test sample is at some arbitrarily warm constant temperature (e.g., 37° C.) when at some later time $t_c$, a cold event (e.g., 10° C.) is induced in the test sample. As expected, the detector signal 31 drops off as the sample cools. The limitations of the cooling/heating cycle are dictated largely by the limitations of the test sample. In the case of living human tissue, a cooling temperature of less than about 0° C. begins to freeze the tissue and a heating temperature of greater than about 40° C. begins to cause discomfort to the patient. This defines the limits of the heating and cooling cycle used for human subjects.

Referring to FIG. 17, for a human subject, using a temperature event of 10° C., after about 500 ms (milliseconds), the gradient penetrates to about 150 μm into the skin. Consequently, referring to FIG. 18, a cooling/heating cycle (also referred to as a driving frequency) of 1 Hz provides information to a depth of about 150 μm. It has also been determined that exposure to a 10° C. cooling event for about 167 ms leads to a gradient that penetrates to a depth of 50 μm (FIG. 17). Therefore, a cooling/heating cycle of 3 Hz provides information to a depth of about 50 μm (FIG. 18). By subtracting the detector signal information measured at a 3 Hz driving frequency from the detector signal information measured at a 1 Hz driving frequency, a picture of skin between 50 and 150 μm emerges.

This concept has particular usefulness when used to make non-invasive measurements of non-uniform or layered samples such as living tissue. The present invention uses a first (fast) driving frequency to induce a shallow temperature gradient and a second (slow) driving frequency to induce deeper gradients. The individual requirements for driving frequencies are determined by test sample and temperatures of the heating and cooling events. The phase information measured at each driving frequency is correlated and processed by a data processing means to accurately determine the analyte concentration.

In human skin the stratum corneum 1610 is 10–30 μm thick and provides little useful information concerning the concentration of blood analytes. However, the underlying derma 1611 and epidermis 1612 contain fluids which contain significant amounts of analytes. The present invention provides a method for determining analyte concentration in the underlying layers 1611, 1612 while compensating for the inaccuracies induced by the overlying stratum corneum 1610.

Figure 19:
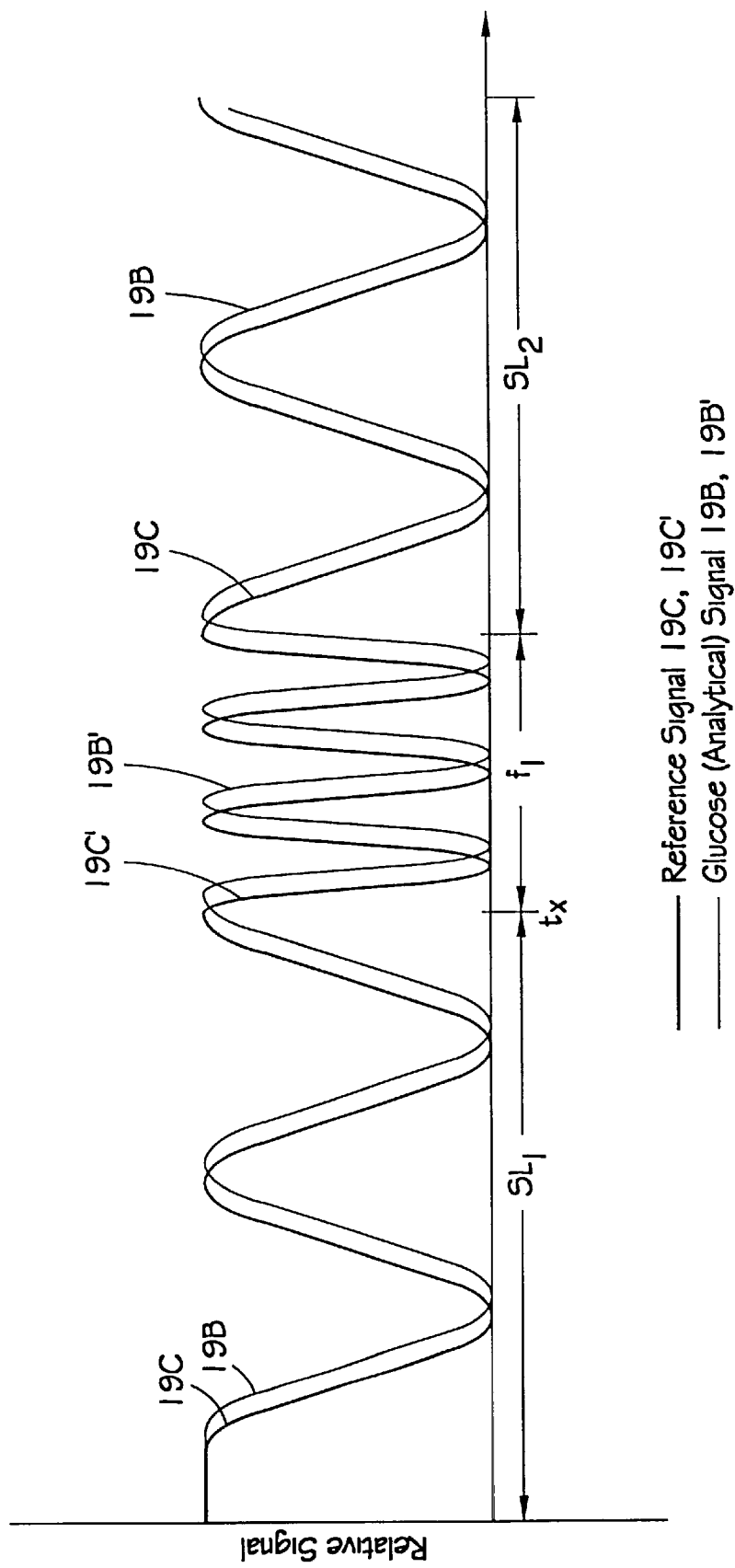
FIG. 19 is a graphical representation of skin response to a two sequential periodically modulated temperature gradients with the y-axis representing relative detector is signal intensity and the x-axis representing the time or phase angle.

The present invention relies on the introduction of two sequentially implemented gradients. Each gradient having a different driving frequency. This embodiment also relies on the detection and measurement of phase differences Ø(λ) between reference 19C, 19C' and analytical 19B, 19B' signals. The present invention measures the phase differences Ø(λ) at both fast (e.g., 3 Hz) and slow (e.g., 1 Hz) driving frequencies. Referring to FIG. 19, a slow cycle (e.g., 1 Hz) provides measurements of analyte concentration in the region from 0 to about 150 μm. An analytical signal 19B is measured and a reference signal 19C is measured. A phase delay Ø(λ) is measured. The phase delay between 19B and 19C (this is similar to the phase delay between the analytical signal 14B and the deep tissue reference signal 14C of FIG. 14) is relatively longer at higher analyte concentrations. The slow driving frequency continues for arbitrarily chosen number of cycles (in region $SL_1$), for example, two full cycles. Then a higher driving frequency (fast cycle) temperature modulation is induced. Due to the higher frequency of the fast cycle (e.g., 3 Hz), only information contained in the shallower regions (e.g., the regions from 0–50 μm) of the skin is measured. An analytical signal 19B' is measured and a reference signal 19C' is measured at the higher driving frequency and the phase delay Ø(λ)' is determined. Since the shallower regions (i.e., the stratum corneum, 10–30 μm thick) have a lower analyte concentration, the phase delay is relatively smaller Ø(λ)'. The fast cycle is also run through a number of cycles (for example, in region $f_1$, e.g., two cycles). By running through the fast and slow cycles a few times, the various phase delays Ø(λ), Ø(λ)' can be integrated over time. In fact, the pattern may be continued for any amount of time. The fast cycle (shallow tissue) phase data Ø(λ)' is subtracted from the slow cycle data Ø(λ), providing an accurate determination of analyte concentration in the region between 50 to 150 μm in depth.

Figure 20:
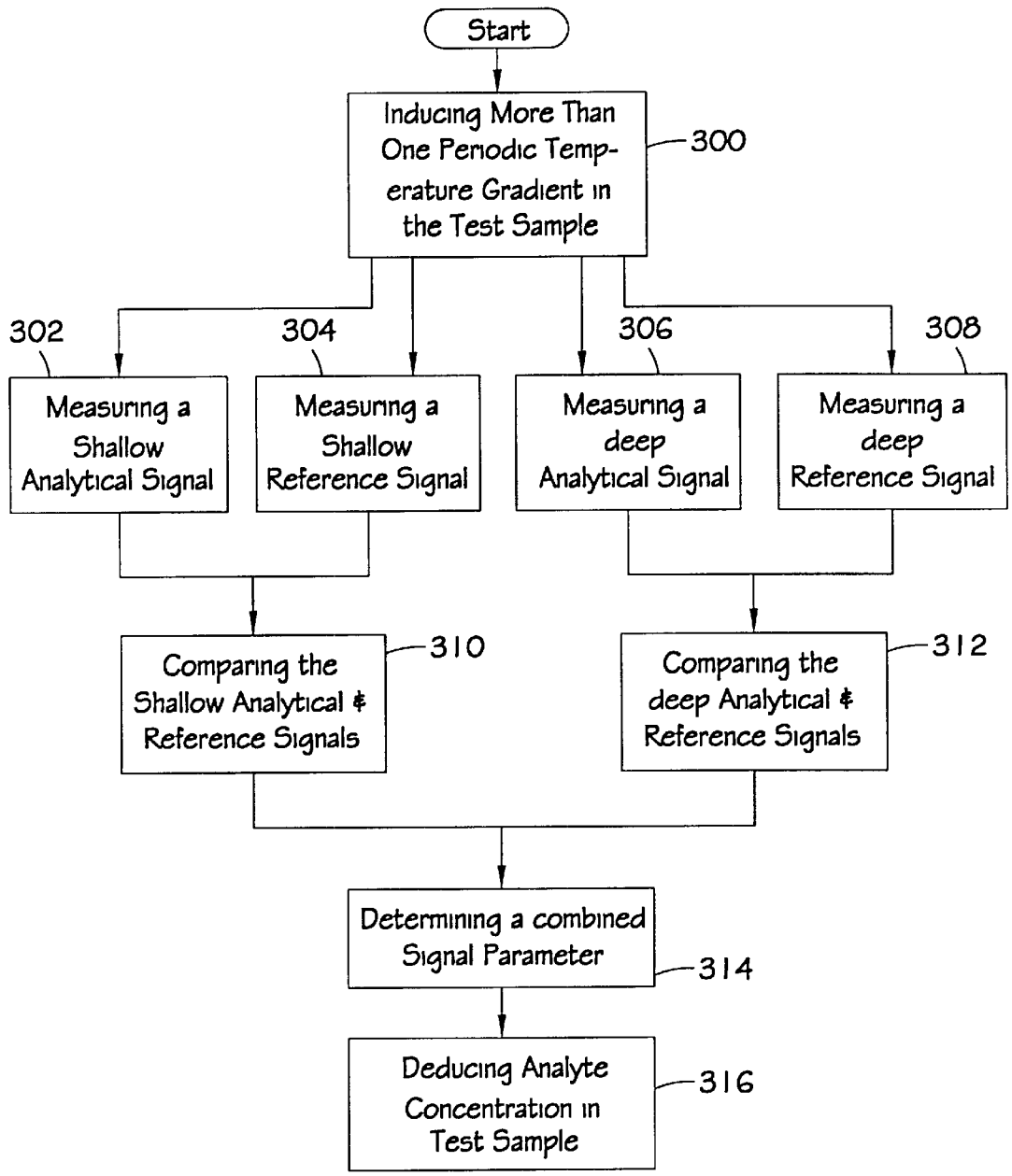
FIG. 20 is a flowchart showing a third embodiment of the present invention.

FIG. 20 is a flowchart depicting an embodiment of the present invention having more than one gradient driving frequency. In Step 300, shallow and deep gradients are cyclically induced in a test sample. In Steps 302, 304, 306, and 308, respectively, measurements are made of a shallow analytical signal 19B', a shallow reference signal 19C', a deep analytical signal 19B, and a deep reference signal 19C. It should be noted that one or more shallow analytical signals 19B', one or more shallow reference signals 19C', one or more deep analytical signals 19B, and a deep reference signals 19C may be measured. In Step 310, the shallow analytical signals 19B' of Step 302 and the shallow reference signals 19C' of Step 304 are compared to form a shallow parameter signal (for example, a shallow phase signal). In Step 312, the deep analytical signals 19B of Step 306 and the deep reference signals 19C of Step 308 are compared to form a deep parameter signal (for example, a deep phase signal). In Step 314 the shallow parameter signal of Step 310 is processed with the deep parameter signal of Step 312 to determine a combined parameter signal. In Step 316 the combined parameter signal of Step 314 is used to deduce the analyte concentration of the test sample.

Figure 21:
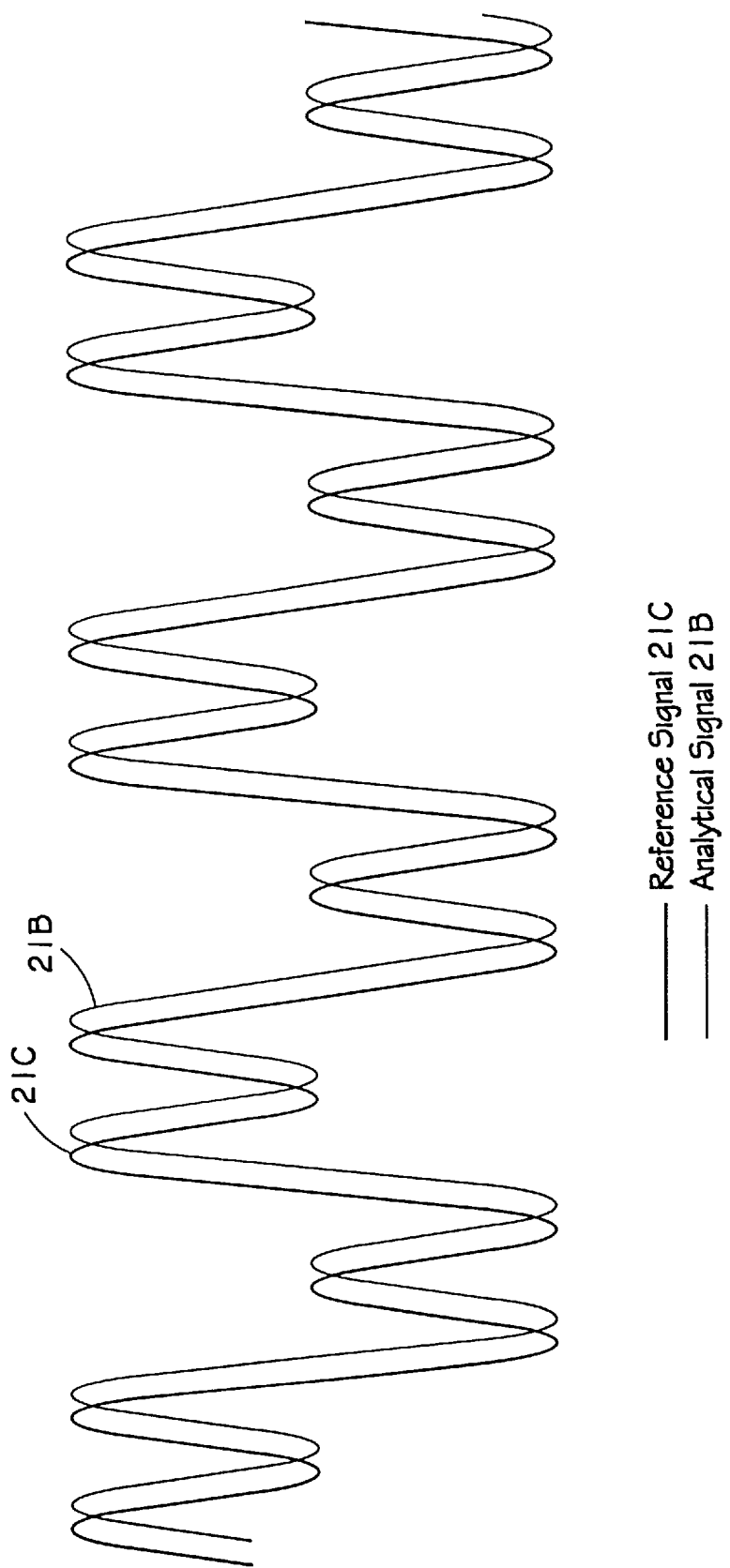
FIG. 21 is a graphical representation of skin response to a two superimposed periodically modulated temperature gradients with the y-axis representing relative detector signal intensity and the x-axis representing the time or phase angle.

Additionally, the two driving frequencies (e.g., 1 Hz and 3 Hz) can be multiplexed as shown in FIG. 21. The fast (3 Hz) and slow (1 Hz) driving frequencies can be superimposed rather than sequentially implemented. During analysis, the signals can be separated by frequency (using Fourier transform or other techniques) using a data processing means and independent measurements of phase delay at each of the two driving frequencies may be calculated. Once resolved, the two signals are processed by a data processing means to determine absorbance and analyte concentration.

E. Embodiment of the Present Invention Using Periodic Gradients Induced at More Than One Driving. Frequency to Non-Invasively Determine Human Blood Glucose Concentration The present invention may be used to quickly, accurately, and non-invasively determine the blood glucose concentration in a human patient. The gradient driving frequencies may be implemented sequentially (as in FIG. 19) or simultaneously (as in FIG. 21). For illustrative purposes the method of FIG. 19 will be used to determine the blood glucose concentration of a human subject. A first driving frequency is induced at about 1 Hz and penetrates deeply into the fluid containing regions of the skin (e.g. about 150 $\mu$m). After a few cycles (preferably two cycles) a second gradient is induced at a second driving frequency. The second frequency is at approximately 3 Hz and induces a shallow gradient which penetrates to just beneath the status corneum. After a few cycles (preferably two cycles) a gradient is again induced at the first frequency. In this way the two driving frequencies are alternated over a test period. The test period can be any length of time, but for convenience, a sixty second test period serves well. It should also be noted that the order of implementation of the first and second driving frequencies can be freely altered.

Referring to FIG. 19, the analytical signals 19B, 19B' are measured at a glucose absorbance peak in the range of 7–10 $\mu$m. For example, the analytical signal may be monitored using the glucose absorbance peak at 9.3 $\mu$m. Reference wavelengths are chosen. As disclosed herein, the signal may be monitored at one or more wavelengths. The reference signal 19C, 19C' shown in FIG. 19 is measured at a water transmission peak, for example, at about 4 $\mu$m. The signal when measured at a transmission peak reflects gradient effects deep within the skin. As with all embodiments more then one reference wavelength may be monitored for increased accuracy.

After the first gradient is induced at a first driving frequency a first analytical signal 19B and a first reference signal 19C are monitored. The first analytical signal 19B and the first reference signal 19C are compared. Based on the comparison, a phase difference between the first analytical signal 19B and the first reference signal 19C is measured. This phase difference forms a first phase signal $\varnothing(\lambda)$. This first phase signal $\varnothing(\lambda)$ measures phase differences deeply into the skin, including the stratum corneum. The first phase signal $\varnothing(\lambda)$ is monitored as the cooling/heating cycle runs for an arbitrary number of cycles, preferably two.

A second gradient is then induced at a higher frequency (e.g. 1 Hz). This high frequency gradient penetrates to just below the stratum corneum. A second analytical signal 19B' and a second reference signal 19C' are monitored. The second analytical signal 19B' and the second reference signal 19C' are compared. Based on the comparison, a phase difference between the second analytical signal 19B' and the second reference signal 19C' is measured. This phase difference forms a second phase signal $\varnothing(\lambda)'$. The second phase signal $\varnothing(\lambda)'$ measures phase in the shallow regions of the skin like the stratum corneum. The second phase signal $\varnothing(\lambda)'$ is monitored as the cooling/heating cycle runs for an arbitrary number of cycles, for example, two or more.

The first and second gradients are measured repeatedly over a test period (e.g. about 5–10 seconds). The first phase signal $\varnothing(\lambda)$ is subtracted from the second phase signal $\varnothing(\lambda)'$ to form a combined phase signal. The combined signal compensates for the effects of the surface and stratum corneum to provide an accurate measure of the phase difference only in the fluid containing regions of the skin, as measured throughout the test period. This combined phase signal information is correlated with previously determined data relating phase to glucose concentration and the concentration of blood glucose in the patient is determined. This patient blood glucose information can be transmitted, as an electrical signal, for further processing.

The present invention discloses a method for measuring radiation absorbance effects and determining analyte concentration in test samples. The procedure has been optimized and illustrated with regard to samples containing large relative quantities of water. The method is widely applicable to homogeneous materials and especially heterogeneous or layered materials provided that useful wavelengths can be identified: (1) a reference wavelength where radiation transmission is high and/or (2) a reference wavelength where radiation transmission is low; (3) analyte absorbance peak where interference with the reference wavelength is low. In particular, the present invention is useful in aqueous systems in the analysis of glucose concentration.

From the foregoing, it will be obvious to one with ordinary skill in the art that application of the principles taught herein provides the following advantages:

providing a method for analyzing liquid or gas or solids or any combination thereof;

providing a method for analyzing heterogeneous or non-uniform sample materials, including semisolids such as biological material;

providing significantly improved resolution over prior methodologies;

providing a :non-invasive method of determining the concentration of low levels of analytes;

providing a highly accurate determination of analyte concentration;

providing a method of determining analyte concentration at varying depths of a sample material;

providing a method of determining local analyte concentration in heterogeneous or non-uniform sample materials;

accurately measuring low analyte concentrations, for example, glucose concentrations in the range of 100 mg/dL or blood ethanol at 0.1%;

measuring, with a high degree of precision and repeatability, analyte concentrations within an acquired data set;

using a periodically varying temperature gradient to gain information regarding analyte concentration;

using phase information to determine analyte concentration;

using continuously integrated phase information in conjunction with the periodically induced temperature gradient to increase measurement accuracy;

using intermittently measured phase information, such as "zero crossings" or signal peaks and troughs, in conjunction with a periodically driven temperature gradient to accurately determine analyte concentration;

using amplitude information to determine analyte concentration;

using continuously integrated amplitude information in conjunction with the periodically induced temperature gradient to increase measurement accuracy;

using intermittently measured amplitude information, such as "zero crossings" or signal peaks and troughs, in conjunction with a periodically driven temperature gradient to accurately determine analyte concentration;

using frequency information to determine analyte concentration;

using continuously integrated frequency information in conjunction with the periodically induced temperature gradient to increase measurement accuracy;

using intermittently measured frequency information, such as "zero crossings" or signal peaks and troughs, in conjunction with a periodically driven temperature gradient to accurately determine analyte concentration.

The present invention has been shown and described with regard to certain preferred embodiments. However, it should be readily apparent to those of ordinary skill in the art that various changes and modifications in form or detail may be made with departure from the spirit and scope of the invention as set forth in the appended claims. In particular, the invention disclosed herein is not limited to detection of ethanol or glucose, but may be used to quantify analyte concentration of a wide variety of analytes.

Furthermore, the invention is not confirmed to use on in-vivo human test subjects. The invention may be used on animals and plants and on in-vitro samples.

Finally, the invention disclosed may be practiced without any element not specifically disclosed herein.

The applicants claim:

1. A method of analyzing a test sample utilizing a radiation detector, comprising the steps of:
    a) providing a test sample;
    b) inducing a thermal gradient in said test sample;
    c) responsive to said inducing step, measuring at least one reference signal emitted by said sample;
    d) further responsive to said inducing step, measuring at least one analytical signal emitted by said sample;
    e) comparing said reference and analytical signals to determine parameter information; and
    f) transmitting said parameter information, as an electrical signal for further processing.

2. A method as in claim 1 wherein said step (e) of comparing said reference and analytical signals to determine parameter information includes comparing said reference and analytical signals to determine phase difference information between said analytical and reference signals.

3. A method as in claim 2 wherein said step of comparing phase difference information includes the step of deducing the analyte concentration of said sample based on said phase difference information.

4. A method as in claim 3 wherein said step of deducing the analyte concentration includes correlating said phase information with known information regarding analyte concentration and phase.

5. A method as in claim 2 wherein said at least one analytical signal is measured at one or more predefined wavelengths.

6. A method as in claim 3 wherein said predefined wavelength intervals are defined by analyte absorbance peaks.

7. A method as in claim 2 wherein said at least one reference signal is measured at one or more predefined wavelength intervals.

8. A method as in claim 7 wherein said predefined wavelength intervals are defined by the absorbance properties of the sample media.

9. A method as in claim 1 wherein said step of inducing a thermal gradient in said test sample includes inducing a periodic thermal gradient in said test sample.

* * * * *